(12) United States Patent
Solomon et al.

(10) Patent No.: US 9,655,933 B2
(45) Date of Patent: May 23, 2017

(54) FILAMENTOUS BACTERIOPHAGE AS AN ANGIOGENESIS MODULATOR

(71) Applicant: RAMOT AT TEL-AVIV UNIVERSITY LTD., Tel Aviv (IL)

(72) Inventors: Beka Solomon, Herzliya (IL); Eyal Dor-On, Ramat Hasharon (IL)

(73) Assignee: RAMOT AT TEL-AVIV UNIVERSITY LTD., Tel Aviv (IL)

( * ) Notice: Subject to any disclaimer, the term of this patent is extended or adjusted under 35 U.S.C. 154(b) by 0 days.

(21) Appl. No.: 14/384,473

(22) PCT Filed: Mar. 15, 2013

(86) PCT No.: PCT/US2013/032043
§ 371 (c)(1),
(2) Date: Sep. 11, 2014

(87) PCT Pub. No.: WO2013/138716
PCT Pub. Date: Sep. 19, 2013

(65) Prior Publication Data
US 2015/0110745 A1    Apr. 23, 2015

Related U.S. Application Data

(60) Provisional application No. 61/715,364, filed on Oct. 18, 2012, provisional application No. 61/611,297, filed on Mar. 15, 2012.

(51) Int. Cl.
*A61K 35/76*    (2015.01)
*C12N 7/00*    (2006.01)

(52) U.S. Cl.
CPC .... *A61K 35/76* (2013.01); *C12N 2795/14132* (2013.01); *C12N 2795/14171* (2013.01); *C12N 2810/10* (2013.01); *C12N 2810/40* (2013.01)

(58) Field of Classification Search
CPC .................................. A61K 35/76; C12N 7/00
USPC ....................................................... 424/93.6
See application file for complete search history.

(56) References Cited

U.S. PATENT DOCUMENTS

| 2007/0098828 A1 | 5/2007 | Gonzalez-Villasenor |
| 2008/0057038 A1 | 3/2008 | Yacoby et al. |
| 2009/0175830 A1* | 7/2009 | Fueyo .................. A61K 48/005 424/93.2 |
| 2009/0317324 A1 | 12/2009 | Solomon et al. |
| 2010/0092519 A1 | 4/2010 | Gorringe et al. |
| 2011/0142803 A1 | 6/2011 | Solomon et al. |

OTHER PUBLICATIONS

Gura (Science. 1997; 278: 1041-1042).*
Dennis (Nature. Aug. 7, 2006; 442: 739-741).*
Dabrowska K et al: "Activity of bacteriophages in murine tumor models depends on the route of phage administration", Oncology Research, 15(4):183-187 (2005).
Dabrowska Krystyna et al: "The effect of bacteriophages T4 and HAP1 on in vitro melanoma migration", BMC Microbiology, 9(1):13 (2009).
Tournaire R et al: "A short synthetic peptide inhibits signal transduction, migration and angiogenesis mediated by Tie2 receptor", EMBO Reports, 5(3):262-267 (2004).
Boratynski Janusz et al: "Preparation of endotoxin-free bacteriophages", Cellular & Molecular Biology Letters, 9(2):253-259 (2004).
Paulina Budynek et al: "Bacteriophages and cancer", Archives of Microbiology, 192(5):315-320 (2010).
Jessica I. Lundin et al: "Endotoxin and Cancer", Environmental Health Perspectives Supplements, 117(9):1344-1350 (2009).
Supplementary European Search Report issued in corresponding European Patent Application No. EP13761938, dated Oct. 26, 2015.

* cited by examiner

*Primary Examiner* — Yan Xiao
(74) *Attorney, Agent, or Firm* — Browdy and Neimark, PLLC

(57) ABSTRACT

The invention relates to a filamentous bacteriophage, carrying bacterial Lipopolysaccharide (LPS) endotoxin on its surface, for use in treating cancer and in inhibiting angiogenesis, and in a different context, for use in promoting angiogenesis in diseases or conditions in which there is insufficient angiogenesis.

21 Claims, 28 Drawing Sheets

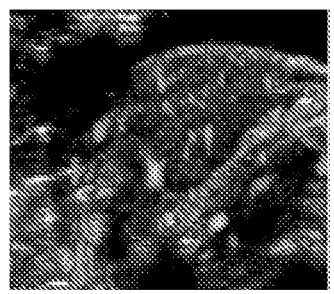
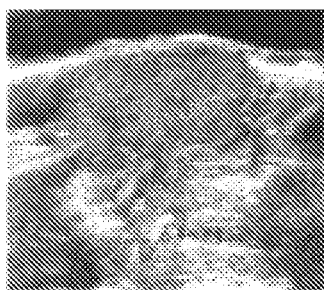
FIG. 7A       FIG. 7B
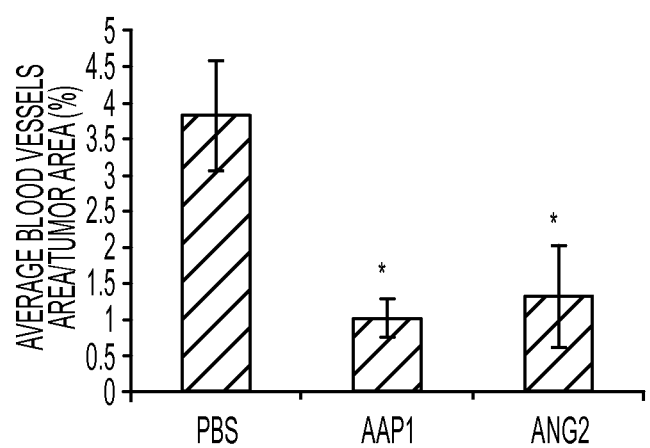
FIG. 7C

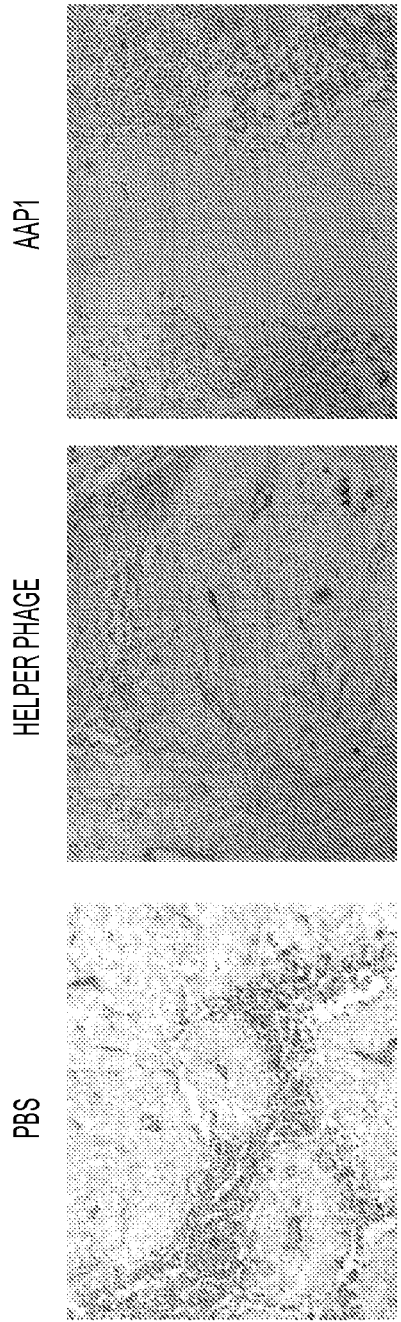
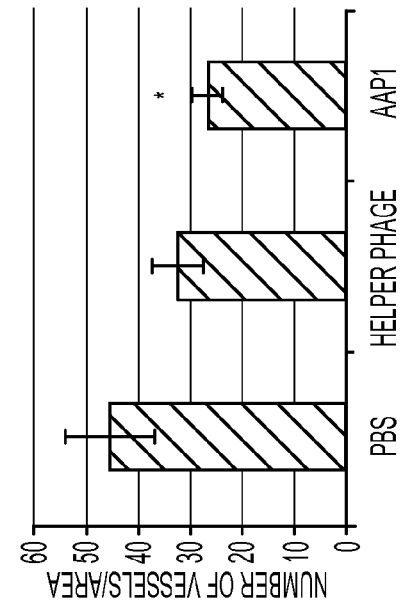
FIG. 8A  FIG. 8B  FIG. 8C  FIG. 8D

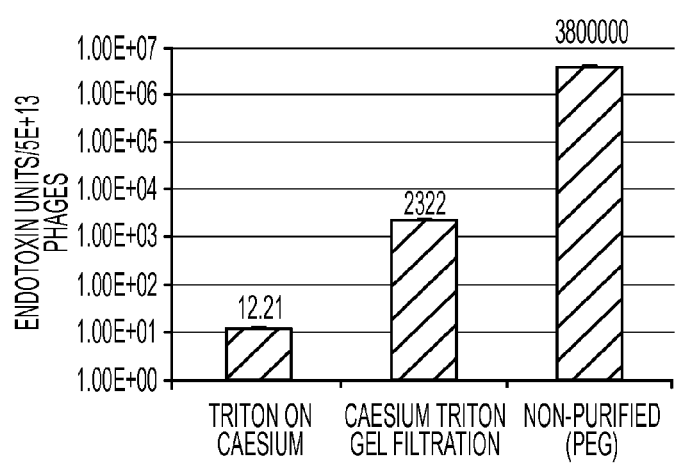
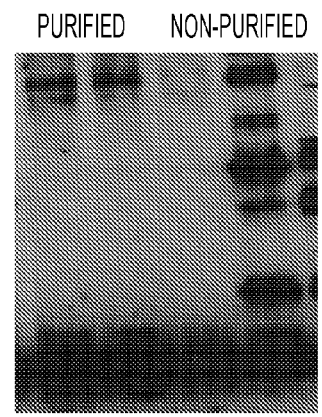
FIG. 9A
FIG. 9B
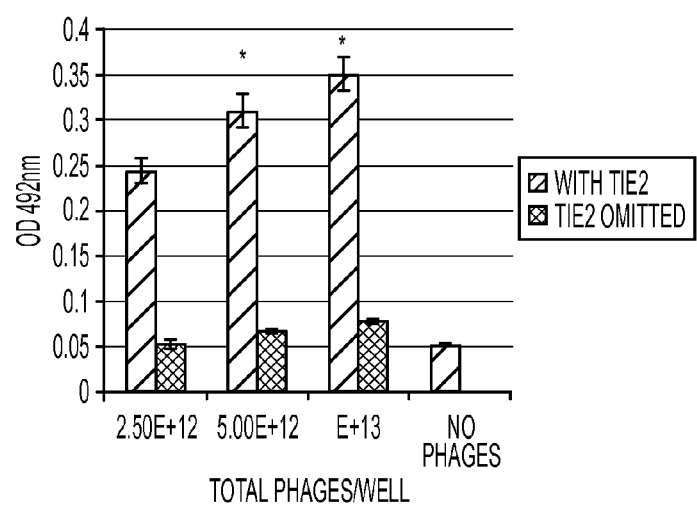
FIG. 10

ANTI-LPS ANTIBODY OMITTED

PHAGES OMITTED

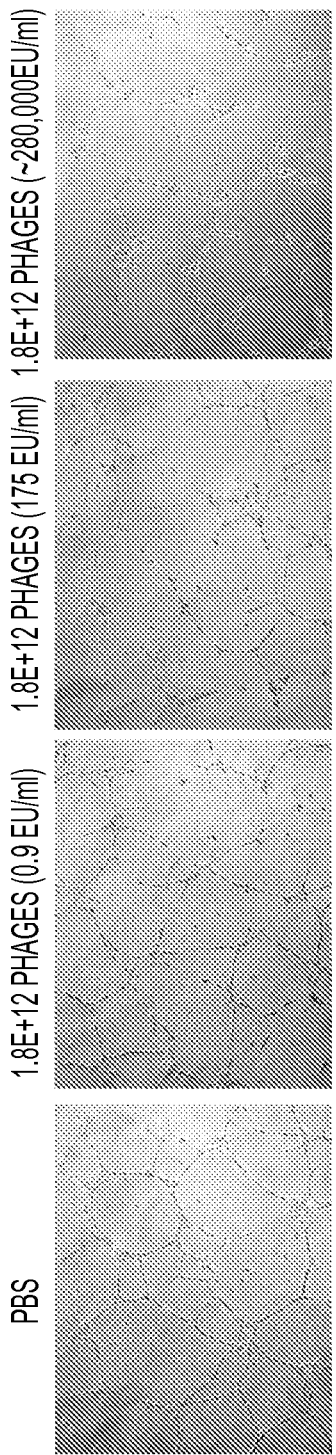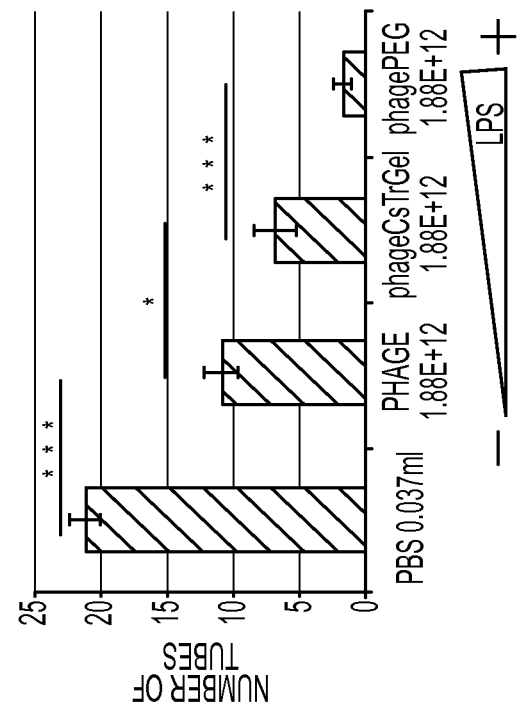

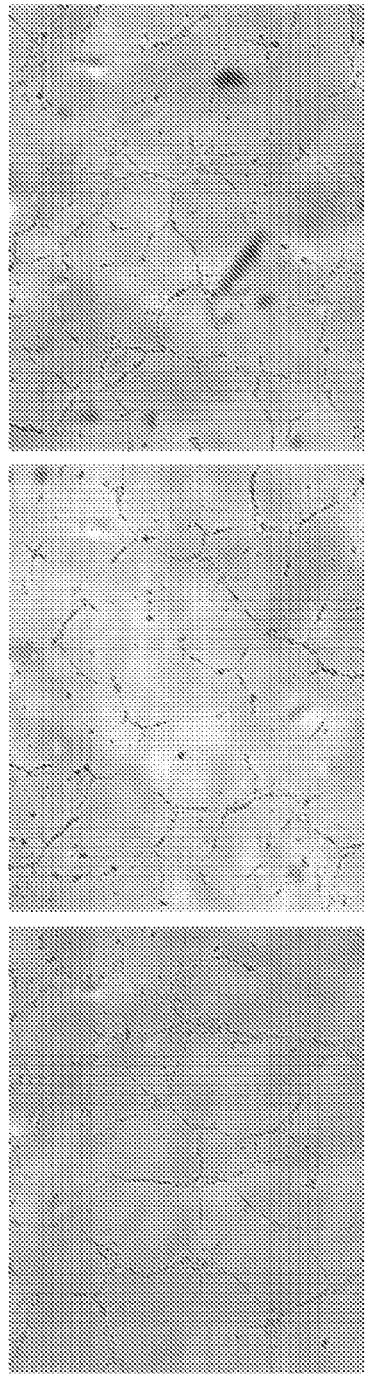
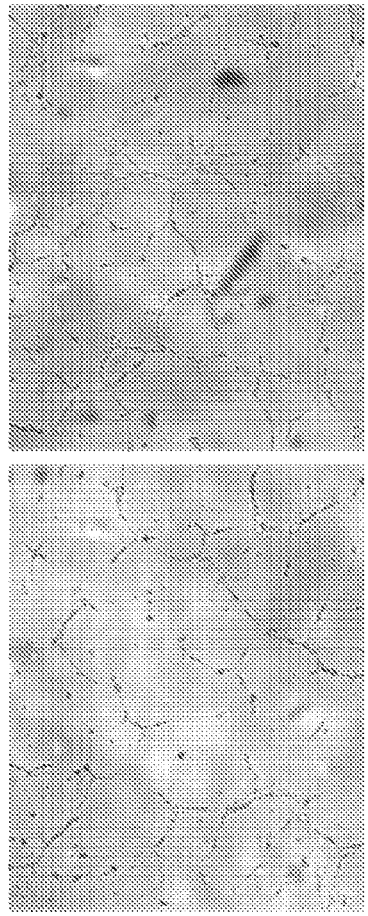
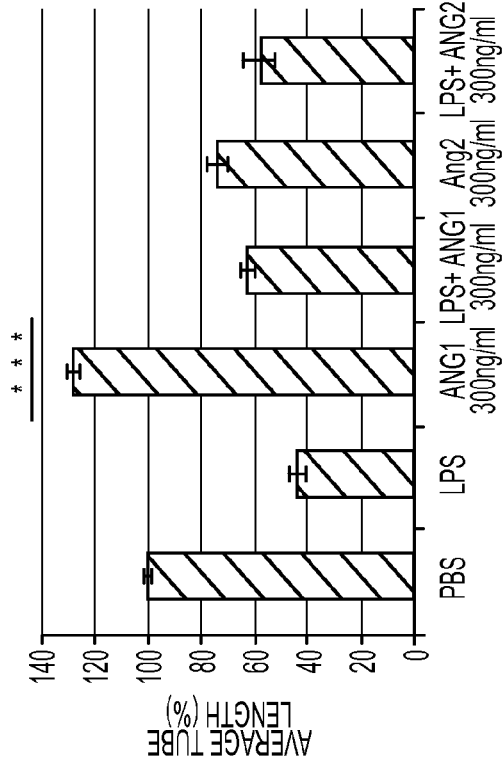
FIG. 20A
FIG. 20B
FIG. 20C
FIG. 20D
FIG. 20E

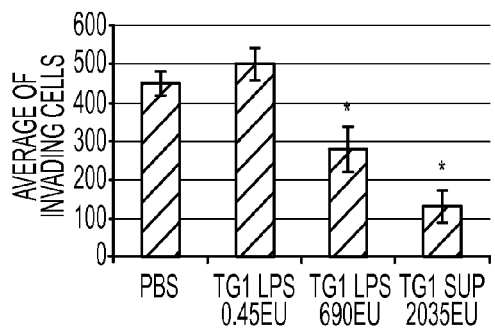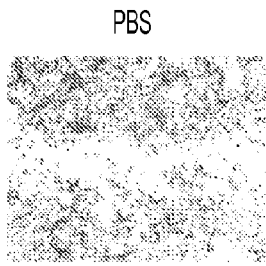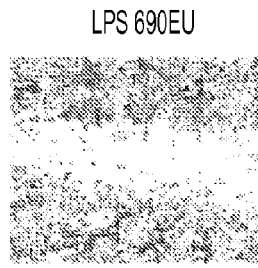
FIG. 21A    FIG. 21B    FIG. 21C
FIG. 22A    FIG. 22B    FIG. 22C
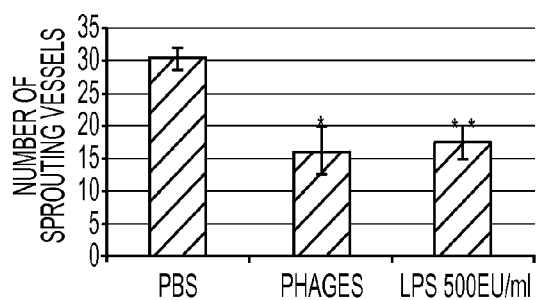
FIG. 22D

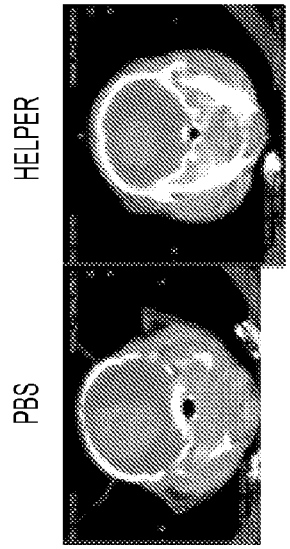
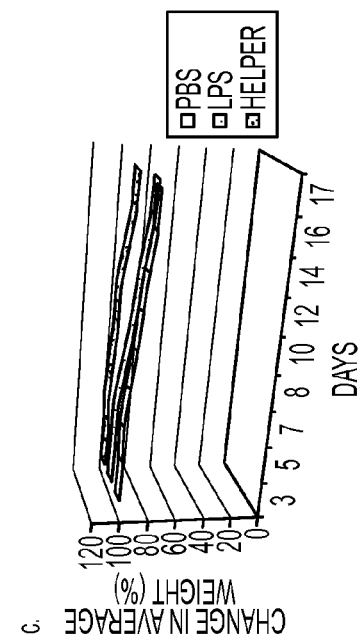
FIG. 29B
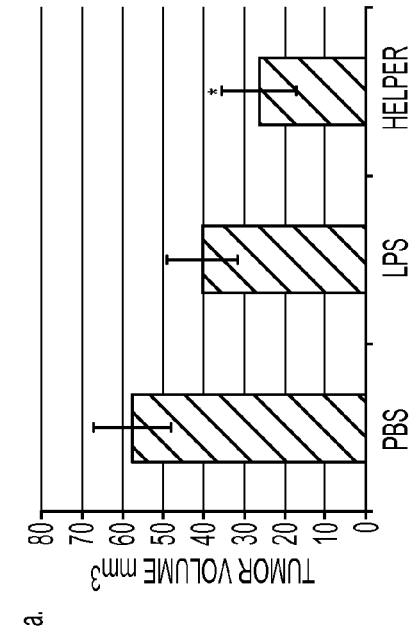
FIG. 29A
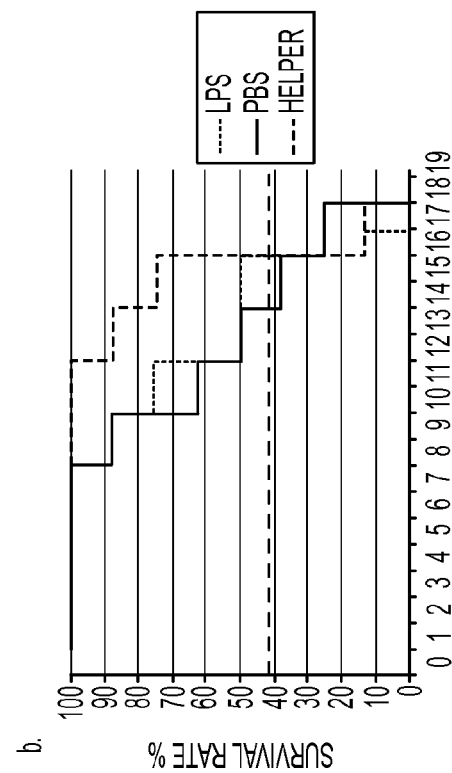
FIG. 29D
FIG. 29C

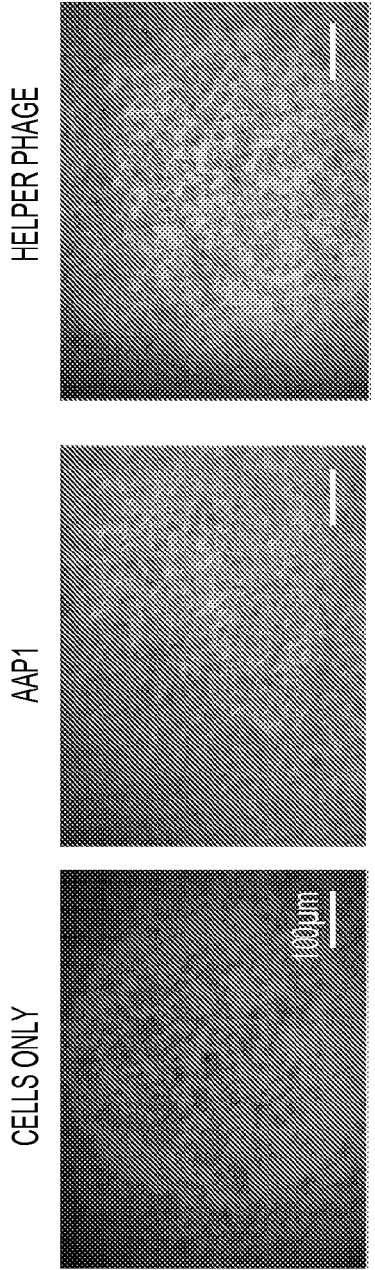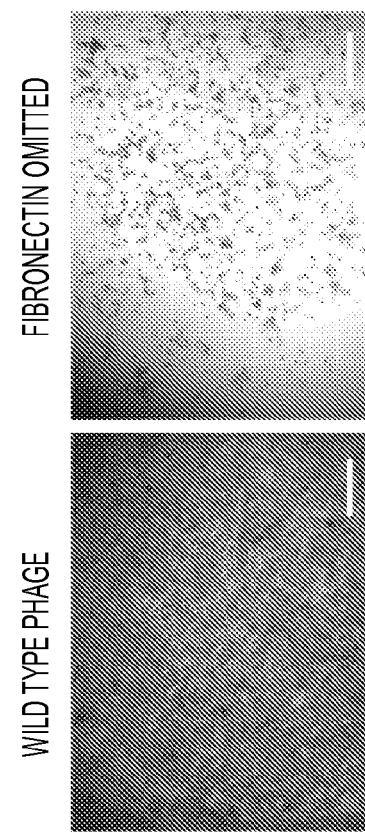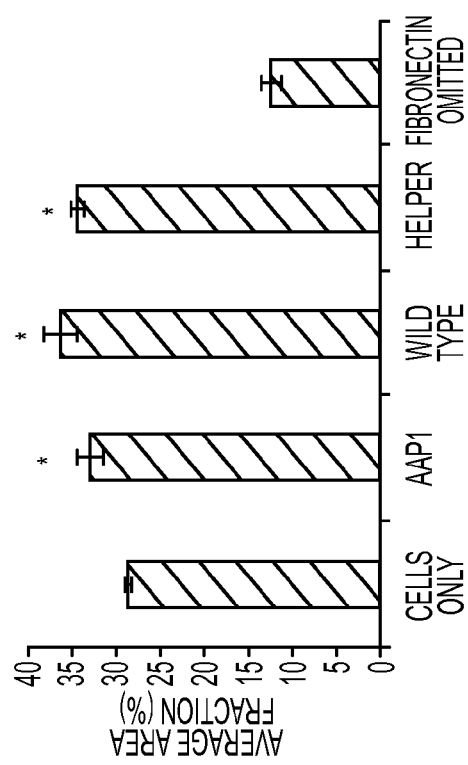
FIG. 32A CELLS ONLY
FIG. 32B AAP1
FIG. 32C HELPER PHAGE
FIG. 32D WILD TYPE PHAGE
FIG. 32E FIBRONECTIN OMITTED
FIG. 32F

FILAMENTOUS BACTERIOPHAGE AS AN ANGIOGENESIS MODULATOR

BACKGROUND OF THE INVENTION

Field of the Invention

The present invention relates to modulation of angiogenesis, such as the inhibition of angiogenesis in cancer and other diseases in which there is excessive angiogenesis and the promotion of angiogenesis in diseases or conditions in which there is insufficient angiogenesis.

Description of the Related Art

Angiogenesis is an intricate progression which takes part in normal states such as embryo development and menstrual cycle but is also related to several pathologies including wound healing, cancer, macular degeneration and ischemia (Risau 1997; Maas et al., 2001; Tonnesen et al., 2000; Kerbel 2008; and Napoleone et al., 2005). More recently, accumulating data links angiogenesis with a broader range of pathologies including inflammatory and neurodegenerative diseases (Beat et al., 2006; Creamer et al., 2003; and Hosoi et al., 2010). Anti-angiogenesis agents such as bevacizumab, sunitinib and sorafenib have already been proven to be beneficial in cancer therapy, especially in combination with chemotherapy (Hurwitz et al., 2004; Sunitinib et al., 2010; and Ghassan et al., 2010), establishing anti-angiogenesis therapy as one of the fourth modality of cancer treatment together with surgery, chemotherapy and radiotherapy.

Many factors that regulate angiogenesis have been identified. It is well established that among them vascular endothelial growth factor (VEGF) and angiopoeitin 1 and 2 (Ang1/2) are key players in modulating the formation of new blood vessels and numerous reports describe the profound effect when their natural balance is disturbed. Ang1 and Ang2 are ligands of Tie2 tyrosine kinase receptor. While Ang1 functions as Tie2 agonist the role of Ang2 is less understood and is generally referred to as a context dependent agonist/antagonist. Signals mediated by Tie2 promote fundamental processes in angiogenesis particularly by manipulating endothelial cells (EC) activity. Notably, Tie2 was demonstrated to induce EC migration, adhesion to extra cellular matrix (ECM) proteins and tube formation. Furthermore, binding of Ang2 or Ang1 to Tie2 modulates vessel stability by either promoting pericytes dissociation from pre-existing quiescent vessels or recruiting pericytes to support nascent vessels respectively (Dvorak, 2005; Huang et al., 2010; and Matijs et al., 2009).

Treatment with filamentous bacteriophage displaying a melanoma tumor-specific peptide (amino acid residues RRKRMTILKSRM (SEQID NO:2) or TRTKLPRLHLQS (SEQ ID NO:3)) or an HLA-A2 specific Fab fragment resulted in regression of established melanoma tumors in mice (Eriksson et al., 2007 and 2009).

Vascular endothelial growth factor (VEGF) displayed on filamentous bacteriophage was combined with a type I collagen scaffold and, in the presence of human microvascular endothelial cells (hMVECs), was shown to promote angiogenesis of hMVECs on the scaffold of phage-VEGF bound collagen (Yoon et al., 2012)

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention provides a method for treating cancer and a method for inhibiting angiogenesis. The method for treating cancer or for inhibiting angiogenesis involves administering to a patient suffering from cancer or in need of inhibition of angiogenesis an effective amount of a filamentous bacteriophage carrying bacterial Lipopolysaccharide (LPS) endotoxin on its surface, optionally displaying on its surface a peptide that binds to Tie2 receptor tyrosine kinase (such as a peptide comprising the amino acid sequence NLLMAAS (SEQ ID NO:1), with the proviso that the filamentous bacteriophage does not display an antibody or a tumor specific peptide (such as a melanoma tumor-specific peptide comprising the amino acid sequence of RRKRMTILKSRM (SEQ ID NO:2) or TRTKLPRLHLQS (SEQ ID NO:3)) on its surface.

The present invention also provides a method for promoting angiogenesis in a disease or condition in which there is insufficient angiogenesis. This method and use involves administering to a patient in need thereof an effective amount of a filamentous bacteriophage carrying bacterial Lipopolysaccharide (LPS) endotoxin on its surface, optionally displaying on its surface a peptide that binds to Tie2 receptor tyrosine kinase, with the proviso that the filamentous bacteriophage does not display vascular endothelial growth factor (VEGF) on its surface.

BRIEF DESCRIPTION OF THE DRAWINGS

FIGS. 7A-7C are Doppler sonograph images of tumors (FIGS. 7A and 7B) and a graph (FIG. 7C) showing inhibition of angiogenesis and a graph in subcutaneous tumors with AAP1 and Ang2.

FIGS. 8A-8D are tissue sections of subcutaneous tumors immunostained with ant-CD31 antibody (FIGS. 8A-8C) and a graph of the number of blood vessels per area (FIG. 8D) for AAP1, helper page and PBS.

FIGS. 9A and 9B are a graph (FIG. 9A) and a Western blot (FIG. 9B) showing the level of endotoxin (LPS) units remaining in stages of phage purification.

FIG. 10 is a graph showing dose dependent binding of helper phage to recombinant human Tie2 receptor in a direct ELISA. The first of each pair of bars is in the presence of Tie2 and the second of each pair of bars is in the absence of Tie2.

FIGS. 19A-19D are images and FIG. 19E is a graph showing inhibition of in vitro angiogenesis by phage is dependent on LPS concentration in the phage preparation.

FIGS. 20A-20D are images and FIG. 20E is a graph showing that LPS inhibits Ang1/Ang2 activity in in vitro HUVEC tube formation.

FIG. 21A is a graph and FIGS. 21B and 21C are images showing LPS inhibits in vitro wound healing.

FIGS. 22A-22C are images and FIG. 22D is a graph showing that phage and LPS inhibit vessel sprouting in an aorta ring assay.

In FIG. 23B, each cluster of bars are from left to right in the descending order of representations as presented to the right of the graph.

FIGS. 29A-29D are graphs (FIGS. 29A and 29D), CT scan (FIG. 29B), and a Kaplan-Meier plot (FIG. 29C) showing that intranasal administration of phage inhibits tumor growth in mice and increases mice survival rate.

FIGS. 32A-32E are images and FIG. 32F is a graph showing that AAP1, wild type filamentous, and filamentous helper phage promote cell adhesion in vitro.

DETAILED DESCRIPTION OF THE INVENTION

Abbreviations

Figure 1:
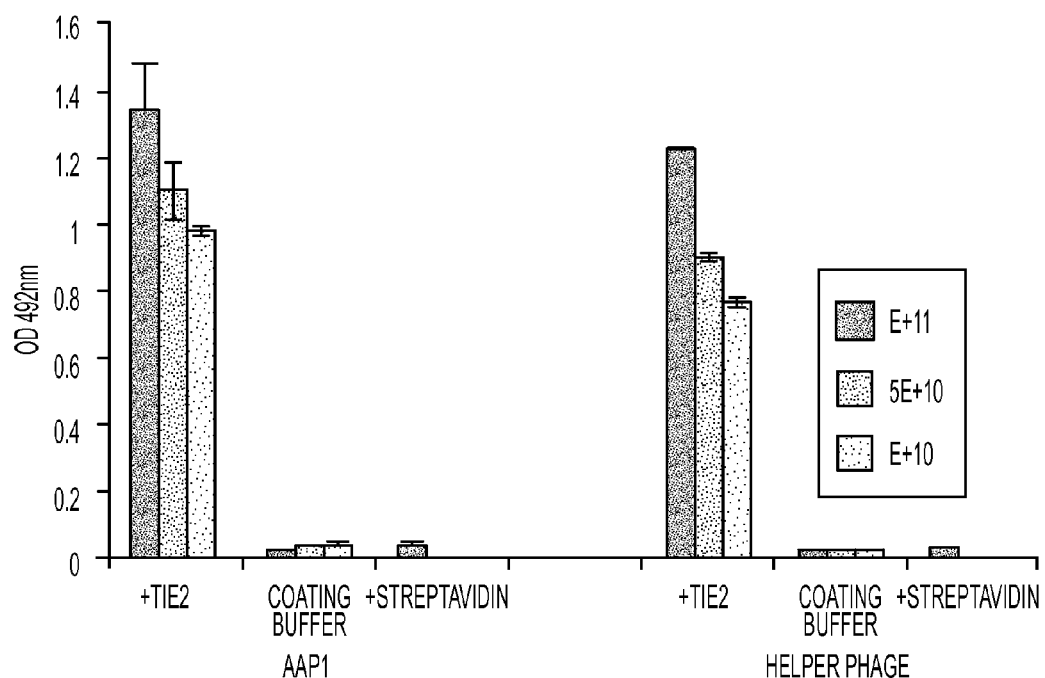
FIG. 1 is a graph showing binding of AAP1 and helper phage at different titers to Tie2, coating buffer and streptavidin.

IN Administration—Intranasal Administration
EC—Endothelial Cells
GBM—Glioblastoma Multiforme
rhAng1—Recombinant Human Angiopoietin 1
rhAng2—Recombinant Human Angiopoietin 2
BBB—Blood Brain Barrier
LLC—Lewis Lung Carcinoma
AAP1—Anti-Angiogenic Phage
LPS—Lipopolysaccharides
CNS—Central Nervous System
GI—Gastrointestinal
HRP—Horseradish Peroxidase
OPD—Ophenylenediamine
HUVEC—Human Umbilical Vein Endothelial Cells
PEG—Polyethylene Glycol
ELISA—Enzyme-Linked Immunosorbent Assay
TEM—Transmission electron microscopy
RPM—Revolution per Minute
FACS—Fluorescence-Activated Cell Sorting
rhLBP—Recombinant Human LPS Binding Protein
LAL—Limulus Amebocyte Lysate
EU—Endotoxin Units
ERK—Extracellular-Signal-Regulated Kinases
MAPK—Mitogen-Activated Protein Kinase
CD—Cluster of Differentiation
H&E—Hematoxylin and Eosin
PBS—Phosphate Buffered Saline
CPM—Counts Per Minute
CT—Computed Tomography
RIPA—Radioimmunoprecipitation Assay
CAM—Chick Chorioallantoic Membrane
GFP—Green Fluorescent Protein The present invention is based on the discovery by the present inventors that the filamentous phage, a gram-negative bacterial virus (Rakonjac et al., 2011), possesses an intrinsic ability to modulate angiogenesis and inhibit tumor growth and show that lipopolysaccharide (LPS), an endotoxin which is anchored to the outer membrane of gram-negative bacteria (Bryant et al., 2010), is attached to the phage surface and contributes to phage anti-angiogenic and anti-tumor activities. Moreover, phage and LPS complexes can interact with Tie2, modulate its phosphorylation and affect downstream signals such as ERK and Akt pathways that are activated during angiogenesis.

It is well known that brain malignancies pose a great challenge for therapeutic intervention because of their sensitive location and the limited access of drugs to the brain due to the blood brain barrier. In particular, glioblastoma multiforme (GBM), which accounts for the majority of the primary brain tumors, is highly difficult to treat with a median survival rate of 1-2 years (Adamson et al., 2009; Baehring et al., 2012). The laboratory of the present inventors previously reported that intranasal (IN) administration of phages resulted in their rapid accumulation in the CNS (Frenkel et al., 2002). Results indicate that phage utilize an extracellular route to gain access to the CNS and plausibly use both the olfactory system and the trigeminal nerve pathways. A prominent advantage of IN administration is that it bypasses the blood brain barrier and the first pass metabolism in the liver, and therefore results in relatively high bioavailability of the desired agent (Chapman et al., 2012). In addition, this route of administration is non-invasive and can be performed by the patients themselves. In the experiments shown in the Examples hereinbelow, the efficacy of IN phage administration in inhibiting brain tumor growth in an aggressive orthotopic GBM model in mice (Ausman et al., 1970; Szatmár et al., 2006) was investigated and it was found that phage significantly inhibited tumor development in mice brains and increased their survival rate by 33%.

The present inventors also demonstrated that approximately 20% of the IN administered phages are inhaled and can be isolated from mice lungs. Lung cancer is the most common and deadliest cancer worldwide accounting for approximately 13% of all cancer cases and 18% of all cancer deaths (Ferlay et al., 2010; who.int/mediacentre/factsheets/). The present inventors established an orthotopic lung tumor model and found that IN administration of phage significantly inhibited lung tumor growth and increased mice survival rate.

It should be noted that the brain serves as a sanctuary for metastasis cells with lung cancer being the primary source of secondary brain tumors (Palmieri et al., 2007; Yamanaka 2009). As such, IN administration of phages to a patient suffering from lung cancer can potentially inhibit lung tumor progression and prevent or inhibit the growth of brain metastasis simultaneously.

As shown in the Examples, the results obtained also demonstrate that the majority of the IN administered phages are swallowed (approximately 55%) and are found in the stomach of mice. Phage isolated from the stomach of mice remained infective, indicating that they survived the extreme conditions of the stomach. Furthermore, phage was isolated from the mice gut and stool samples (Goren et al., 2007), implying that they travel throughout the digestive tract. This opens the door to a potential treatment of gastrointestinal (GI) cancers such as stomach or colorectal cancers via IN or oral administration of phages. GI cancers, in particular stomach, liver and colorectal malignancies are the most deadliest cancers worldwide following lung cancer (Ferlay et al., 2010; who.int/mediacentre/factsheets/).

To increase phage efficacy in inhibiting tumor progression, the present inventors constructed a recombinant phage by cloning a known anti-angiogenic peptide (NLLMAAS; SEQ ID NO:1) (Tournaire et al., 2004) to the major coat protein of the phage. This short peptide was demonstrated to bind to Tie2 receptor and inhibit its activity and was shown to inhibit angiogenesis in vitro and in vivo. This new phage which displays the recombinant protein on all of its major coat proteins (roughly 2700 copies) is termed Anti Angiogenic Phage 1 (AAP1).

The present invention provides a method for treating cancer and, more generally, a method for inhibiting angiogenesis. The method for treating cancer or for inhibiting angiogenesis involves administering to a patient suffering from cancer or in need of inhibition of angiogenesis an effective amount of a filamentous bacteriophage carrying bacterial Lipopolysaccharide (LPS) endotoxin on its surface, optionally displaying on its surface a peptide that binds to Tie2 receptor tyrosine kinase (such as a peptide comprising the amino acid sequence NLLMAAS (SEQ ID NO:1), with the proviso that the filamentous bacteriophage does not display an antibody or a tumor specific peptide (such as a melanoma tumor-specific peptide comprising the amino acid sequence of RRKRMTILKSRM (SEQ ID NO:2) or TRT-KLPRLHLQS (SEQ ID NO:3)) on its surface. A patient in need of inhibition of angiogenesis is one whose vascular endothelium in an organ or tissue is characterized by a non-resting, stressed state and by excessive angiogenesis. The filamentous phage used in the treating cancer and in inhibiting angiogenesis is expected to work in a context dependent manner. It is anti-angiogenic in the context of cancer, where the vascular endothelium in the cancer tissue (where Tie2 is overexpressed) is in a stressed state with conditions favorable for angiogenesis. Thus, the context favors pro-antigenesis, leading to excessive angiogenesis, which needs to be inhibited.

Non-limiting preferred examples of cancers to be treated using filamentous phage are cancers of the brain, lung stomach and other parts of the upper gastrointestinal tract, such as the esophagus and liver, and the lower gastrointestinal tract, such as the colon and rectum. A most preferred example of a cancer of the brain is glioblastoma. In addition, non-limiting examples of diseases in which it is desirable to inhibit angiogenesis include a skin disease such as psoriasis, warts, allergic dermatitis, keloid scars, pyogenic granulomas, blistering disease, Kaposi's sarcoma, and systemic sclerosis; a disease of the nasal or oral cavity, lung, and the gastrointestinal tract such as periodontal disease, primary pulmonary hypertension, asthma, nasal polyps, chronic airway inflammation, cystic fibrosis, inflammatory bowel disease (ulcerative colitis), peritoneal adhesions, and liver cirrhosis; and others such as multiple sclerosis, diabetic retinopathy, diabetic nephropathy, endometriosis, ovarian cysts, uterine bleeding, arthritis, and osteomyelitis, etc (Carmeliet, 2005 including supplemental information).

In a different context (where there is insufficient angiogenesis), the present invention also provides a method for promoting angiogenesis in such a disease or condition in which there is insufficient angiogenesis. This method and use involves administering to a patient in need thereof an effective amount of a filamentous bacteriophage carrying bacterial Lipopolysaccharide (LPS) endotoxin on its surface, optionally displaying on its surface a peptide that binds to Tie2 receptor tyrosine kinase, with the proviso that the filamentous bacteriophage does not display vascular endothelial growth factor (VEGF) on its surface. In this context of insufficient angiogenesis, the filamentous phage is expected to act in a pro-angiogenic manner to promote angiogenesis and serve to treat the disease or condition.

Non-limiting examples of such a disease or condition in which there is insufficient angiogenesis include stroke, hair loss, gastric or oral ulcerations, diabetic ulcers, Crohn's disease, chronic wounds, lupus, preeclampsia, nephropathy, etc (Carmeliet, 2005 including supplemental information).

For purposes of this specification and the accompanying claims, the following definitions apply.

The terms "patient", "subject" and "recipient" are used interchangeably. They include humans and other mammals which are the object of therapeutic treatment.

The term "treating" with respect to cancer is intended to mean substantially inhibiting, slowing or reversing the progression of cancer.

The term "antibody" as used herein includes polyclonal antibodies, monoclonal antibodies, antibody compositions with polyepitope specificities, bispecific antibodies, diabodies, or other purified preparations of antibodies and recombinant antibodies. The antibodies can be whole antibodies, e.g., of any isotype (IgG, IgA, IgE, IgM, etc.), or antibody fragments that bind the antigen of interest. In a specific example of an antibody used in the present invention, the antibody to be formulated is an antibody having the IgG isotype. Antibodies can be fragmented using conventional or other techniques and the fragments screened for binding to an antigen of interest. Generally, an antibody fragment comprises the antigen-binding and/or the variable region of an intact antibody.

The term "antibody fragment" includes segments of proteolytically cleaved or recombinantly prepared portions of an antibody molecule that can selectively bind to a selected protein. Non-limiting examples of such proteolytic and/or recombinant fragments include Fab, F(ab')2, Fab', Fv, and single chain antibodies (scFv) containing a VL and/or VH domain joined by a peptide linker, domain antibodies (dAbs), Nanobodies® (antibody-derived biological therapeutic agents that contain the unique structural and functional properties of naturally-occurring heavy-chain antibodies), and UniBodies (antibodies lacking the hinge region). The scFvs may be covalently or noncovalently linked to form antibodies having two or more binding sites.

As used herein, a "pharmaceutical composition" refers to a preparation of one or more of the active ingredients described herein with other chemical components such as physiologically suitable carriers and excipients. The purpose of a pharmaceutical composition is to facilitate administration of an active ingredient to a patient.

The phrases "physiologically acceptable carrier" and "pharmaceutically acceptable carrier," which may be interchangeably used, refer to a carrier or a diluent that does not cause significant irritation to an organism and does not abrogate the biological activity and properties of the administered active ingredient.

The term "excipient" refers to an inert substance added to a pharmaceutical composition to further facilitate administration of an active ingredient. Non-limiting examples of excipients include calcium carbonate, calcium phosphate, various sugars and types of starch, cellulose derivatives, gelatin, vegetable oils and polyethylene glycols.

The term "wild type filamentous bacteriophage" as used herein means a naturally occurring filamentous bacteriophage that is designated in the art as being wild type.

The term "wild type-like filamentous bacteriophage" as used herein means a filamentous bacteriophage which is not exactly "wild type" but does not display any foreign peptides or proteins on its surface, such as helper phages, a non-limiting example of which is the commercially available M13KO7 helper phage (New England Biolabs, Beverly, Mass.).

The term "inactivated wild type filamentous bacteriophage" as used herein means a wild type filamentous bacteriophage that is not genetically altered by recombinant DNA means, but has been rendered incapable of replication, such as by UV-irradiation. Any mechanism which renders the phage incapable of replication, but does not disturb the filamentous structure of the bacteriophage (retains its ability to penetrate into the brain through the olfactory pathway) is contemplated by this invention.

The term "WT phage" refers to both wild-type filamentous bacteriophage and inactivated wild-type filamentous bacteriophage.

Filamentous bacteriophages (phages) are a group of structurally related viruses which contain a circular single-stranded DNA genome. They do not kill their host during productive infection. The phages that infect *Escherichia coli* containing the F plasmids are collectively referred to as Ff bacteriophages. They do not infect mammalian cells. The filamentous bacteriophage is independently selected from filamentous phages M13, f1, fd and mixtures thereof.

Herein the term "active ingredient" refers to the preparation of the filamentous bacteriophage accountable for the biological effect. Techniques for formulation and administration of active ingredients, e.g., drugs, may be found in "Remington's Pharmaceutical Sciences," Mack Publishing Co., Easton, Pa., latest edition, which is incorporated herein by reference.

Suitable routes of administration of the filamentous bacteriophage according to the present invention may, for example, include topical, oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular injections.

Alternatively, one may administer a preparation in a local rather than systemic manner, for example, via injection of the preparation directly into the brain of a patient or via localized topical application.

The filamentous bacteriophage may be formulated in a pharmaceutical composition and may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredient of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredient may be dissolved or suspended in suitable liquids, such as fatty oils, liquid paraffin, or liquid polyethylene glycols. In addition, stabilizers may be added. All formulations for oral administration should be in dosages suitable for the chosen route of administration.

In addition, oral administration can be also be effected by mixing a phage preparation with food for ingestion by the patient. The oral route can serve to infect the microflora in the gastrointestinal (GI) tract (e.g., *E. coli*) with the administered/ingested phage so that the phage replicates in indigenous GI microflora to produce more phage to treat GI tract pathologies, particularly in the lower GI tract.

For buccal administration, the compositions may take the form of tablets or lozenges formulated in conventional manner.

For administration by nasal inhalation (e.g., intranasal administration), the active ingredient for use according to the present invention are conveniently delivered in the form of an aerosol spray presentation from a pressurized pack or a nebulizer with the use of a suitable propellant, e.g., dichlorodifluoromethane, trichlorofluoromethane, dichlorotetrafluoroethane or carbon dioxide. A nasal spray, which does not require a pressurized pack or nebulizer as in an inhalation spray, can alternatively used for intranasal administration. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredient to allow for the preparation of highly concentrated solutions.

Alternatively, the active ingredient may be in powder form for constitution with a suitable vehicle, e.g., sterile, pyrogen-free water based solution, before use.

The active ingredient may also be formulated in rectal compositions such as suppositories or retention enemas, using, e.g., conventional suppository bases such as cocoa butter or other glycerides.

Pharmaceutical compositions suitable for use in the context of the present invention include compositions wherein the active ingredient is contained in an amount effective to achieve the intended purpose. More specifically, a therapeutically effective amount means an amount of active ingredient effective to treat cancer or inhibit angiogenesis in a patient suffering from cancer or in need of inhibition of angiogenesis or effective to promote angiogenesis in a patient suffering from a disease or condition in which there is insufficient angiogenesis. The cancers to be treated by the filamentous bacteriophage or pharmaceutical composition containing this active ingredient include, but are not limited to brain, lung and stomach cancers, as well as cancers of the nasal and oral cavities and the upper gastrointestinal tract, such as cancer of the esophagus, and the lower gastrointestinal tract, such as the small intestine, colon and rectum. A preferred embodiment of brain cancer is a glioblastoma (GBM).

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

The amount of bacterial LPS endotoxin carried on the filamentous bacteriophage should be more than 100 endotoxin units/$2\times10^{12}$ filamentous bacteriophage or, in other units, more than about 10 ng LPS/$2\times10^{12}$ filamentous bacteriophage. Preferably, the amount of bacterial LPS endotoxin carried on the filamentous bacteriophage is about 430 endotoxin units/$1.7\times10^{12}$ filamentous bacteriophage.

In another aspect of the invention, soluble bacterial LPS endotoxin (i.e., not carried on phage) can be used to treat lung cancer or a cancer of the gastrointestinal tract, preferably formulated for intranasal administration. The dosage in endotoxin units for administration to a cancer patient would be in a similar range to the total endotoxin units that would otherwise be carried on filamentous bacteriophage in the titer of filamentous bacteriophage used for administration.

Toxicity and therapeutic efficacy of the active ingredient described herein can be determined by standard pharmaceutical procedures in vitro, in cell cultures or experimental animals. The data obtained from these in vitro and cell culture assays and in animal studies can be used in formulating a range of dosage for use in human. The dosage may vary depending upon the dosage form employed and the route of administration utilized. The exact formulation, route of administration and dosage can be chosen by the individual physician in view of the patient's condition. (See, e.g., Fingl et al, in "The Pharmacological Basis of Therapeutics", Ch. 1 p. 1 (1975)).

Dosage amount and interval may be adjusted individually to provide plasma, brain, local tissue or tumor levels of the filamentous bacteriophage which are sufficient to treat the cancer, inhibit angiogenesis or promote angiogenesis (minimal effective concentration, MEC). The MEC will vary for each preparation, but can be estimated from in vitro data. Dosages necessary to achieve the MEC will depend on individual characteristics and route of administration. Binding assays can be used to determine plasma concentrations.

Dosage intervals can also be determined using the MEC value. Preparations should be administered using a regimen, which maintains plasma or tissue levels above the MEC for 10-90% of the time, preferable between 30-90% and most preferably 50-90%.

Depending on the severity and responsiveness of the condition to be treated, dosing can be of a single or a plurality of administrations, with course of treatment lasting from several days to several months or until cure is effected or diminution of the disease state is achieved.

The amount of a composition to be administered will, of course, be dependent on the subject being treated, the severity of the affliction, the manner of administration, the judgment of the prescribing physician, etc.

The filamentous bacteriophage composition for treating cancer, for inhibiting angiogenesis or for promoting angiogenesis may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

Having now generally described the invention, the same will be more readily understood through reference to the following examples which are provided by way of illustration and are not intended to be limiting of the present invention.

EXAMPLE 1

Helper Phage and AAP1 Bind to Recombinant Tie2 Receptor

AAP1 or M13K07 Helper Phage (New England Biolabs, Beverly, Mass.) were produced in *Escherichia coli* DH12S or TG1 cells respectively and purified by PEG precipitation. ELISA plate was coated with recombinant Tie2-FC (R&D) 4 µg/ml or with streptavidin 2 µg/ml in coating buffer or coating buffer only. The plate was blocked with 3% milk and incubated with phages for 1 hour at 25° C. Phages were detected with rabbit anti-M13 antibody (our laboratory preparation, 1:2500) followed by goat anti rabbit HRP conjugated antibody (Jackson, 1:2500) and developed with OPD (Sigma). Both phages bound to recombinant Tie2-FC in a dose dependent manner. The results in FIG. 1 show bound phage/well and are expressed as mean values±SME.

Helper Phage and AAP1 Inhibit Tube Formation In Vitro

Figure 2:
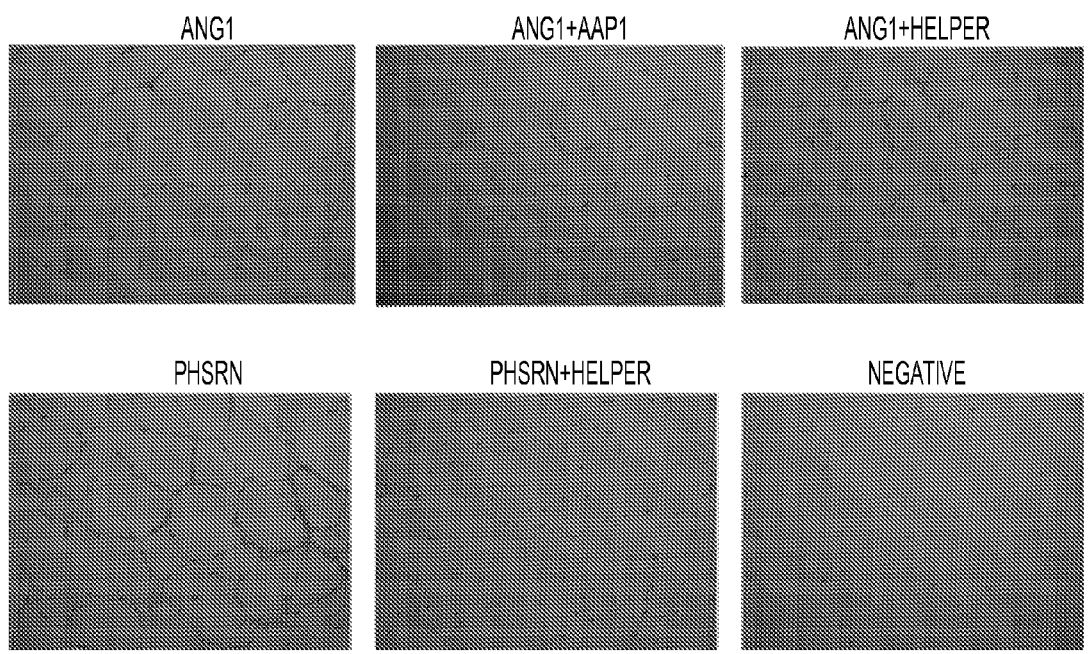
FIG. 2 presents images showing helper phage and AAP1 inhibiting tube formation in vitro.
Figure 3:
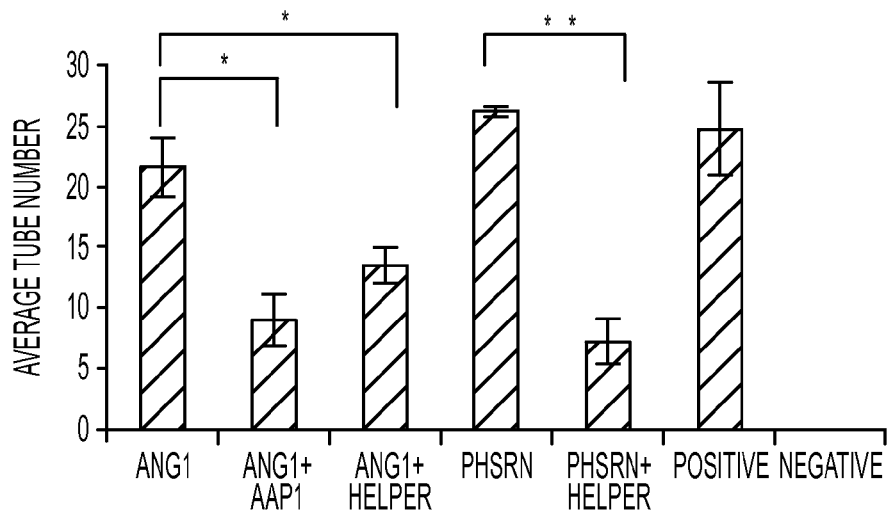
FIG. 3 is a graph showing the average number of tube formation with angiogenic stimulators Ang1 and PHSRN in the presence or absence of AAP1 or helper phage.

HUVEC (Lonza, $3 \times 10^4$ cells per well) were seeded on Matrigel (growth factors reduced, 50 µl/well; 10 mg/ml) coated 24 well plate and were supplemented with 1.8E+12 helper phage or AAP1 together with the angiogenic stimulators Ang1 (Huang et al., 2010) (300 ng/ml) or Ac-PHSRN-NH2 (Peptide2, 1 µg/ml) peptide (Aota et al., 1994) suspended in EGM2 (complete growing media containing optimal growth factors, Lonza). After 8 hours, cell structures were recorded and closed tube formations were counted. Both phages significantly inhibited tube formation induced by either Ang1 or PHSRN. Results are shown in FIGS. 2 and 3, with the results in FIG. 3 being expressed as mean values±SME. Positive control—cells only in EGM2, Negative control—Matrigel omitted (*P<0.05, **P<0.01).

Helper Phage and AAP1 Inhibit Wound Healing In Vitro

Figure 4:
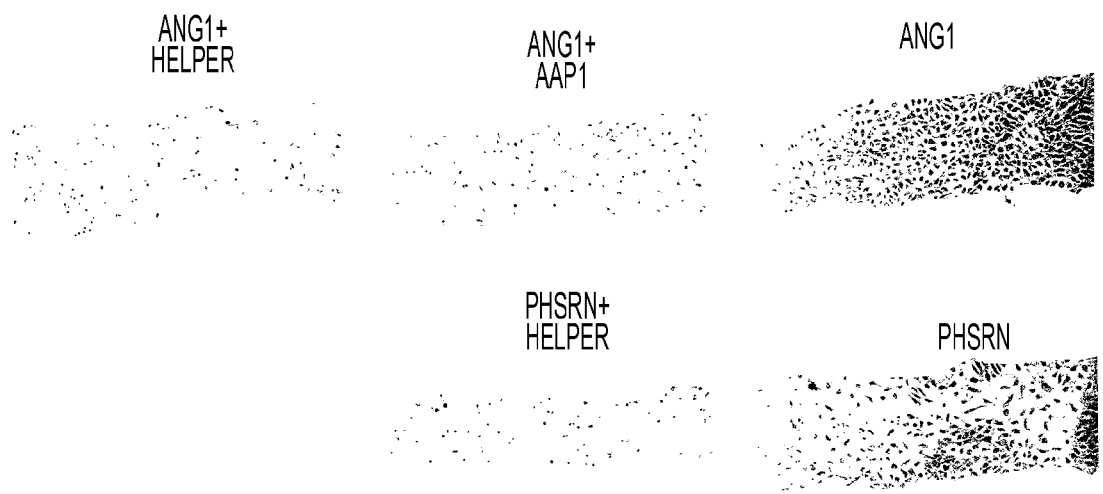
FIG. 4 presents images showing helper phage and AAP1 inhibiting wound healing in vitro.
Figure 5:
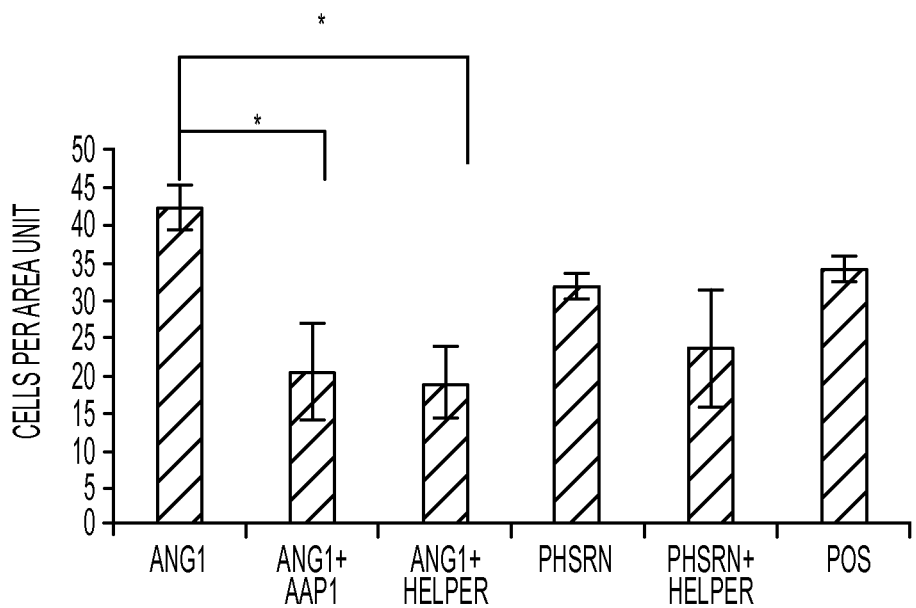
FIG. 5 is a graph showing cells per area unit with angiogenic stimulators Ang1 and PHSRN in the presence or absence of AAP1 or helper phage.

HUVEC ($5 \times 10^5$) were seeded in 6 well plate. Monolayer confluent cells were then scratched to form a gap in the middle of the plate and images were taken. Wells were then supplemented with Helper phages or AAP1 (5E+12) with Ang1 or Ac-PHSRN-NH2 in EGM2. After 13 hours, the plates were recorded and the number of cells invading the gap was counted using the ImageJ software. As shown in FIGS. 4 and 5, significantly fewer cells in the gap area were visualized in wells supplemented with either Helper phage or AAP1 compared with wells treated with the activators Ang1 or Ac-PHSRN-NH2 only. Pos—positive control, cells only in EGM2. Results in FIG. 5 are expressed as mean values±SME (*P<0.05).

Figure 6:
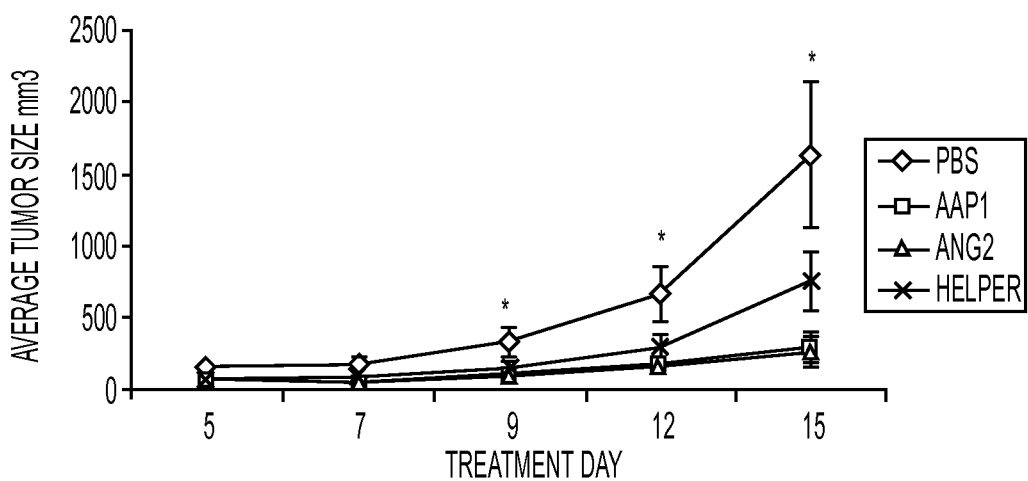
FIG. 6 is a graph showing average tumor size from treatment with AAP1, Ang2, helper phage and PBS control.

Helper Phage, AAP1 and Ang2 Reduce Tumor Mass In Vivo and Inhibit Angiogenesis in Subcutaneous Tumors C57BL/6 female mice (n=6) bearing subcutaneous GBM GL261 tumors were treated with either 1.7E+12 Helper phage, AAP1, PBS or Ang2 3 µg/ml (positive control) on every second day by peritumoral injections. Tumors dimensions were measured by a caliper and tumor volume was calculated using the formula: width$^2$×length*0.5. The graph in FIG. 6 depicts a significant reduction in average tumor volume in mice treated with either AAP1 or Ang2 compared with the PBS control. Results are expressed as mean values±SME. (*P<0.05)

In vivo imaging of subcutaneous tumors using Doppler sonography was performed via Sequoia (ACUSON). Reduction in blood vessels area was visualized in tumors treated with AAP1 or Ang2 compared to PBS treated tumors (FIGS. 7A and 7B). Results in FIG. 7C are expressed as mean values±SME (*P<0.05 as compared to PBS).

Paraffin histology sections of subcutaneous tumors were immunostained with anti-CD31 antibody. Fewer blood vessels were observed in phages treated tumors compared to tumors treated with PBS (FIGS. 8A-8D). Results in FIG. 8D are expressed as mean values±SME (*P<0.05 as compared to PBS).

Phage Purification

To reduce bacteria debris and LPS contamination in the phage preparations, several purification steps were performed. PEG purification results in phage preparation that consists of high LPS and other bacterial contaminations concentration (also referred to as non-purified phage). To obtain a higher grade of purification, Cesium gradient was applied on PEG purified phage which fractionates the preparation on the basis of molecular density. This can be further optimized by incubation of the Cesium purified phage fractions with TRITON X-114 (Sigma) at 56° C. for two hours followed by gel filtration to eliminate TRITON traces (or two sequential ultracentrifugation at 50,000 RPM). This eliminates most of the production impurities and reduces endotoxin levels ~1500 times compared to non-purified phages (LAL assay on the left). However, by incubating PEG purified phages with TRITON X-114 for 12 hours, and then performing a Cesium gradient followed by ultracentrifugation to eliminate TRITON traces, highly purified phage (reduction of endotoxin levels ~150000 times compared with non-purified phage; FIG. 9A) in addition to a drastic reduction in other production impurities were obtained (Western blot; FIG. 9B). However, high purification grade of phages resulted in reduction in the final concentration of the phage, and became non-applicable in some experiments.

Conclusions

A recombinant phage termed Anti-Angiogenic Phage 1 (AAP1) was constructed by cloning the short anti-angiogenic peptide sequence NLLMAAS (SEQ ID NO:1) (Tournaire et al., 2004) to the major coat protein of a phage with a single copy of the major coat protein gene. This resulted in a display of roughly 2700 copies of this peptide on each phage. The present inventors show that AAP1 can bind to recombinant human Tie2 in ELISA and affects endothelial cells (EC) activity in vitro. It is also demonstrated that AAP1 can significantly inhibit subcutaneous GBM allografts growth which was accompanied by reduction in angiogenesis in vivo as demonstrated by Doppler sonography. This was also supported by immunohistology analysis with antibodies against CD31. However, the helper phage, which has a wild type-like phenotype (M13KO7 Helper Phage, New England Biolabs) and served as a negative control, was observed to also bind to rhTie2 and affect EC activity and tumor growth. The present inventors therefore focused on understanding the nature of the helper phage anti-angiogenic and anti-tumorigenic activities.

EXAMPLE 2

Phages Bind to Tie2 and Ang2

An ELISA plate was coated with either rhTie2 (4 µg/ml) in coating buffer or coating buffer alone. Different concentrations of Helper phages (PEG purified) were applied to the plate. Phages were detected by anti-p8 antibodies HRP conjugated and the dose dependent binding of phage to recombinant human Tie2 receptor in a direct ELISA is shown in FIG. 10 with results expressed as mean±SEM (*P<0.05 as compared to 2.5E+12 phages).

Figure 11:
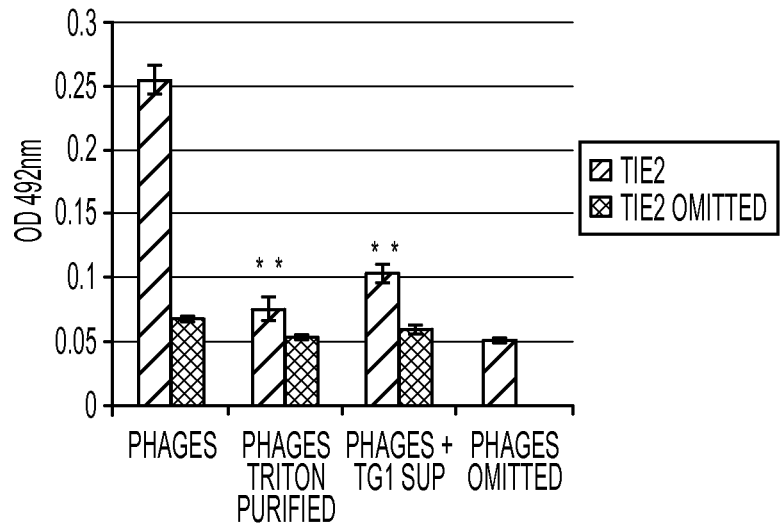
FIG. 11 is a graph of ELISA results showing helper phage binding to Tie2 is compromised by LPS removal or competition with LPS containing bacteria. Left bar of pairs is with Tie2 and right bar of pairs is without Tie2.

An ELISA was performed as previously described. 5E+12 of either PEG purified phages, triton purified phages or PEG purified phages supplemented with 45% TG1 supernatant were applied to the plate. The results in FIG. 11 show phage binding to Tie2 being compromised by LPS removal or competition with LPS containing bacteria supernatant, with the results expressed as mean±SEM (**P<0.01 as compared to PEG purified phages alone).

Figure 12:
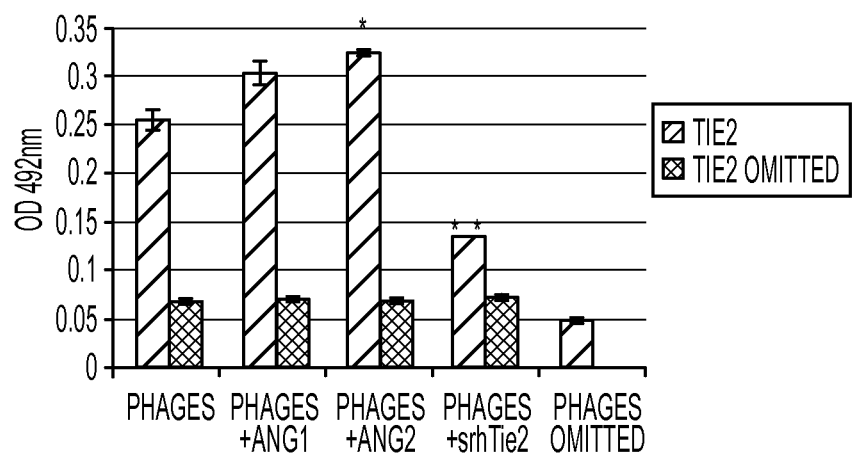
FIG. 12 is a graph of ELISA results showing that soluble Tie2 competes with helper phage over binding to immobilized Tie2. Left bar of pairs is with Tie2 and right bar of pairs is without Tie2.

Another ELISA was performed as previously described. 5E+12 of PEG purified phages with or without 4 µg of soluble recombinant human Ang1, Ang2 or Tie2 were applied to the plate. The results in FIG. 12 show that soluble Tie2 competes with phage over binding to immobilized Tie2 with possible interaction between Ang1/2 and phage, with the results expressed as mean±SEM (*P<0.05,**P<0.01 as compared to phage alone).

Figure 13:
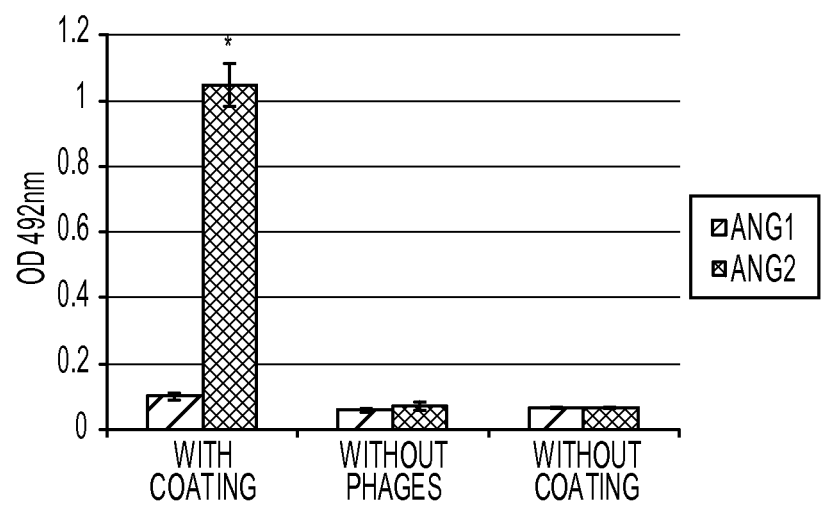
FIG. 13 is a graph of ELISA results showing helper phage binds to Ang2 but not to Ang1. Left bar of pairs is with Ang1 and right bar of pairs is with Ang2.

An ELISA plate was coated with either rhAng2 or rhAng1 (4 µg/ml) in coating buffer or coating buffer alone. Helper phages (PEG purified) were applied to the plate. Phages were detected by anti-p8 antibodies HRP conjugated. The results in FIG. 13 show the phage binds to Ang2 but not to Ang1, the results expressed as mean±SEM (*P<0.05 as compared to samples without phages or without coating protein).

LPS is Attached to Filamentous Phages

Figure 14A:
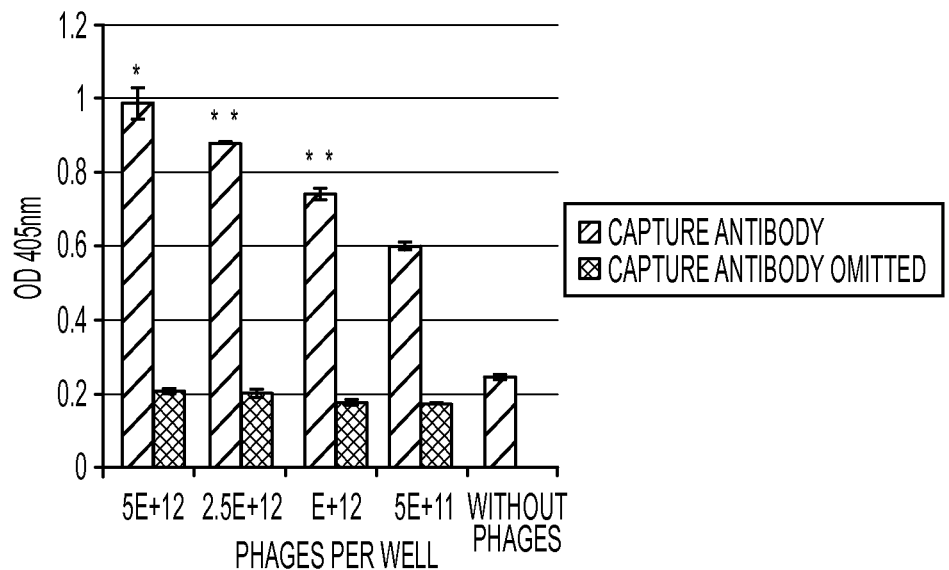
FIGS. 14A and 14B are graphs of ELISA showing co-localization of LPS (detected with anti-LPS antibodies) and phage (detected with anti-P3 capture antibodies) in FIG. 14A and LPS localization on page, using capture antibodies, is dependent on phage purification. Left bar of pairs is with capture antibody and right bar of pairs is without capture antibody.

PEG purified phages were captured by anti-p3 antibodies. LPS was detected by anti-LPS antibodies followed by Alkaline phosphatase conjugated antibodies. FIG. 14A shows co-localization of LPS and filamentous phage in a sandwich ELISA with the results expressed as mean±SEM (*P<0.05, **P<0.01 as compared between two sequential doses).

Figure 14B:
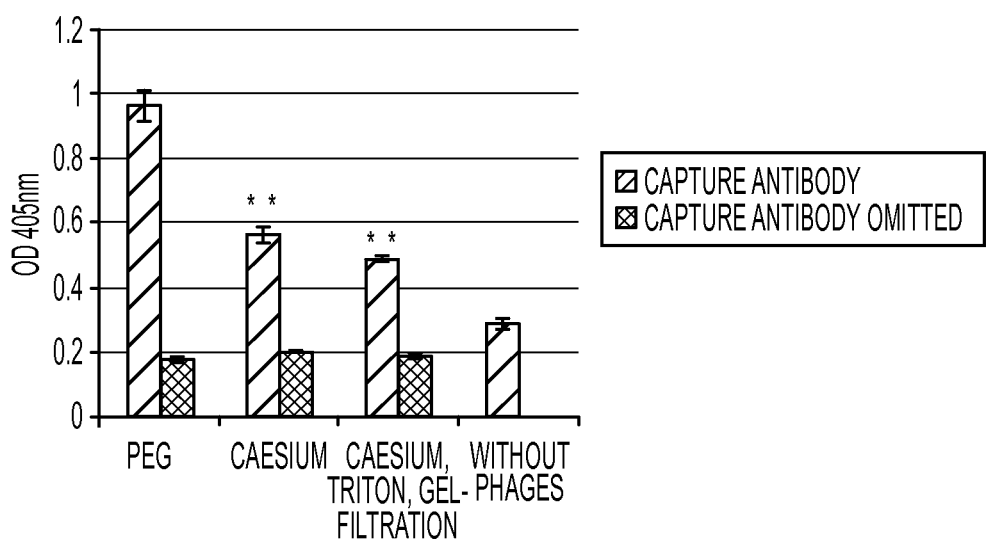
Figure 15A:
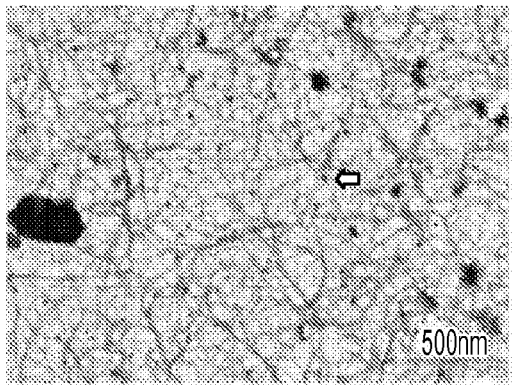
FIGS. 15A-15F are transmission electron microscopy (TEM) images of co-localization of LPS and filamentous phage in sandwich ELISA based immunogold TEM with anti-p8 capture antibodies.
Figure 15B:
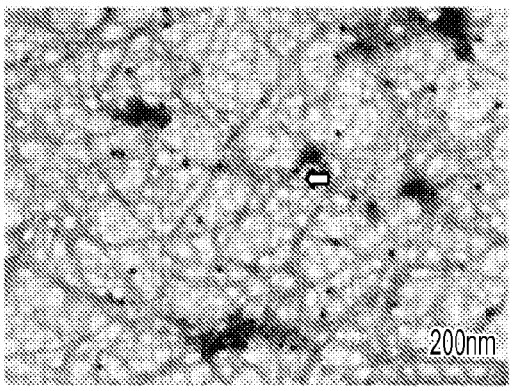
Figure 15C:
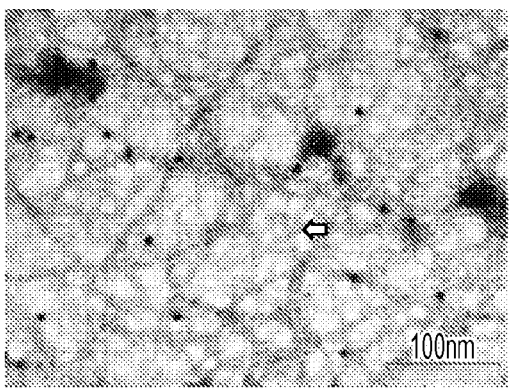
Figure 15D:
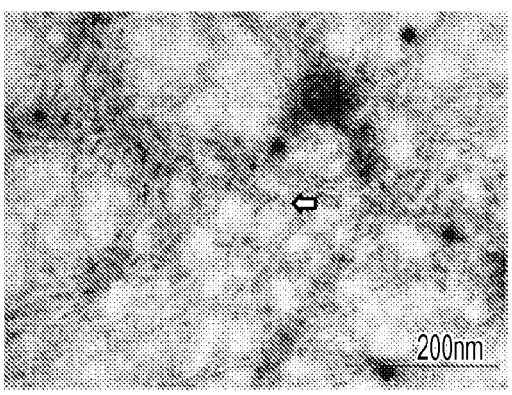
Figure 15E:
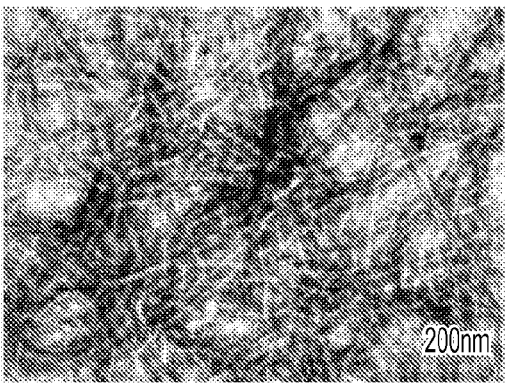
Figure 15F:
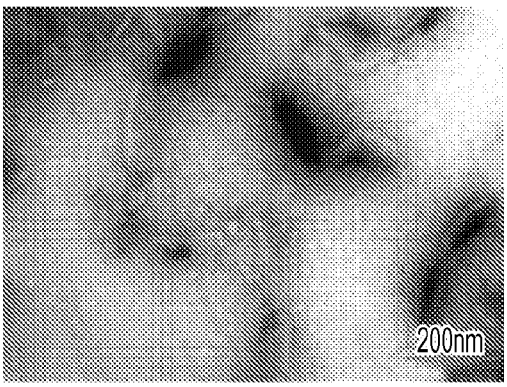

ELISA was performed as previously described. Phage at different purification grades were applied to the plate. FIG. 14B shows LPS localization on phage is dependent on the phage purification grade with the results expressed as mean±SEM (**P<0.01 as compared to PEG purified phages).

FIGS. 15A-15F show co-localization of LPS and filamentous phage in a sandwich ELISA-based immunogold TEM. PEG purified phages were immobilized to a nickel grid by anti-p8 capture antibodies. LPS was detected by anti-LPS antibodies followed by gold conjugated antibodies (arrow). The images in FIGS. 15A-15D are presented in increasing magnification.

Figure 16A:
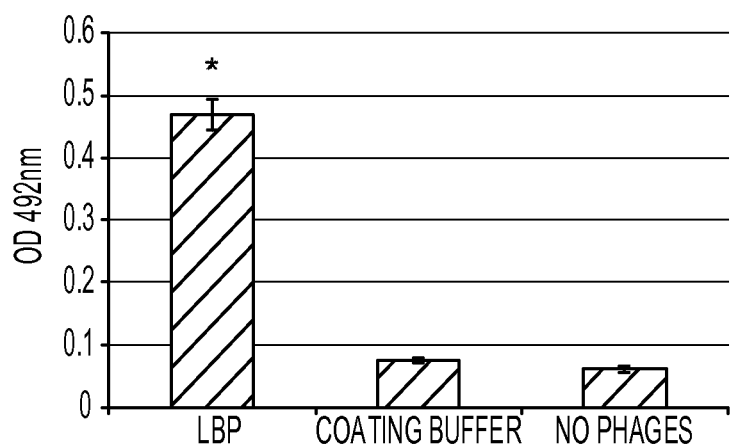
FIGS. 16A and 16B are graphs showing that phage binds to LPS binding protein in a direct ELISA (FIG. 16A) and the quantification of LPS carried by phage (FIG. 16B). The left bar of pairs in FIG. 16B is with capture antibody and right bar of pairs is without capture antibody.

FIG. 16A shows that phage binds to LPS binding protein in a direct ELISA. The ELISA plate was coated with 4 µg/ml of rhLBP. E+13 phages were applied to the plate and detected by anti-p8 HRP conjugated antibody, with the results expressed as mean±SEM (*P<0.05 as compared to controls).

Figure 16B:
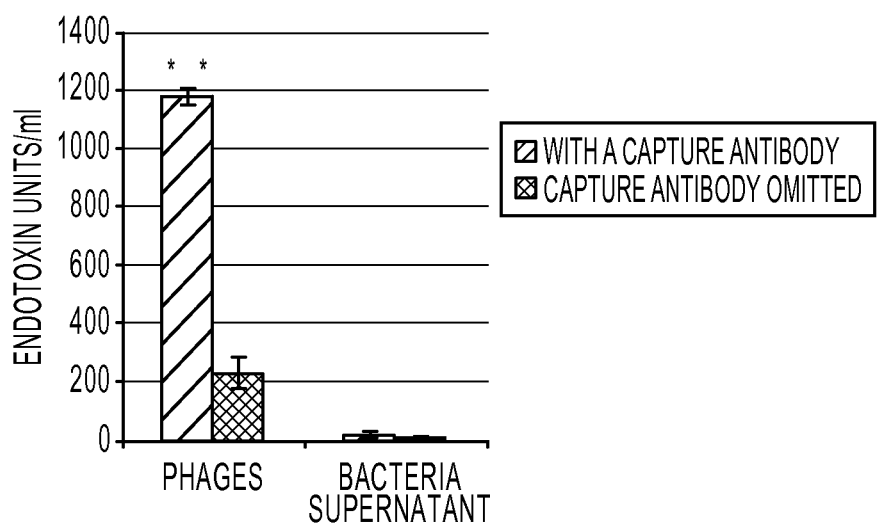

An ELISA plate was coated with anti-p8 capture antibody or coating buffer alone. Samples of either 2E+12 of PEG purified phage or supernatant of non-infected bacteria growth in a total volume of 0.1 ml were added for 1 hour at room temperature and plate was thoroughly washed. To detect bacteria endotoxin in the immobilized phages the complex was detached by incubation with NaOH over night at room temperature and samples were taken to the Limulus amebocyte lysate (LAL) assay. Assuming that all phages in the sample were immobilized to the capture antibody and detached by treatment with NaOH, 2E+12 phages carry at least 100 endotoxin units which are roughly 10 ng of LPS. FIG. 16B shows the quantitation of LPS carried by phage, where the results are presented as mean±SEM (**P<0.01 as compared to control without a capture antibody).

LPS and Phages Modulate Tie2 and ERK Phosphorylation Levels

Figure 17B:
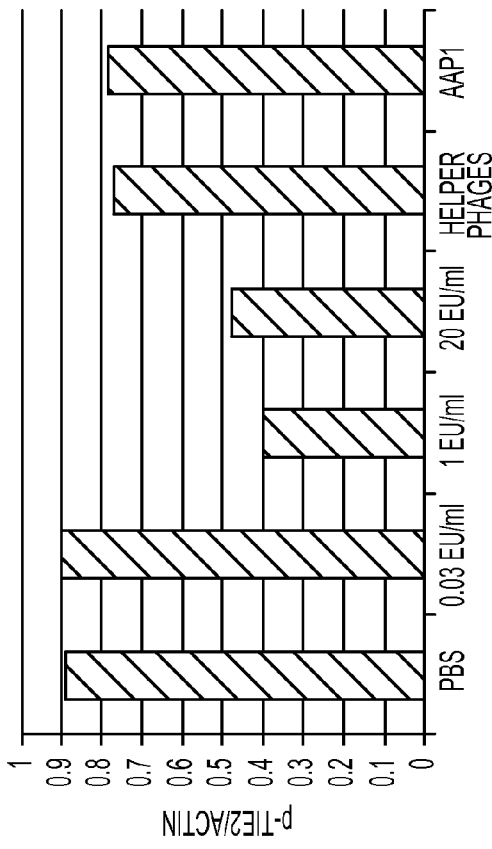
FIGS. 17A-17D are Western blots (FIGS. 17A and 17C) and graphs (FIGS. 17B and 17D) showing that LPS or phage reduces the levels of phosphorylated Tie2 and ERK in HUVEC.
Figure 17D:
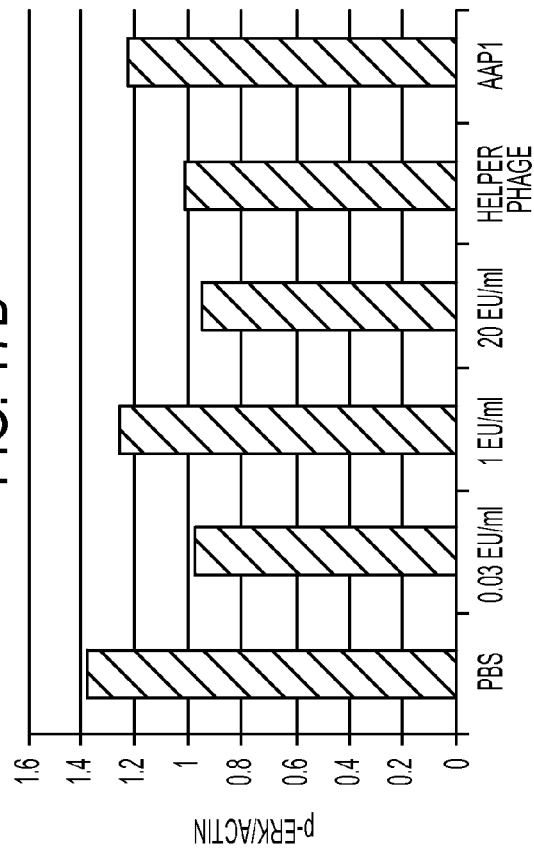
Figure 17A:
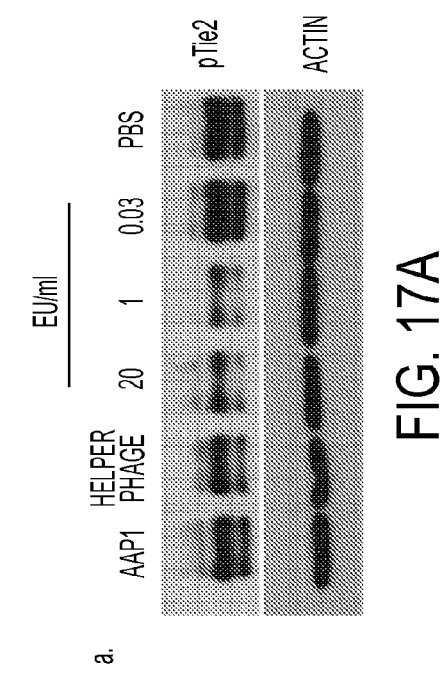
Figure 17C:
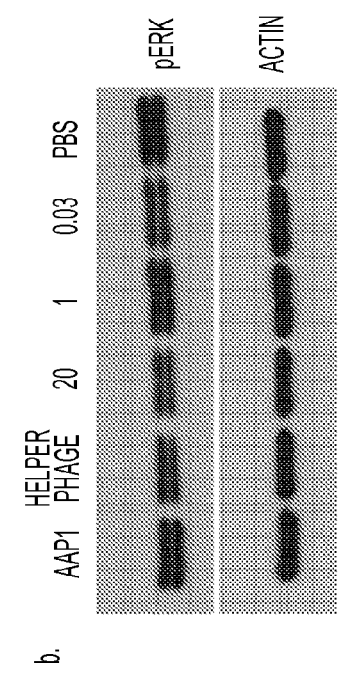

FIGS. 17A-17D are Western blots (FIGS. 17A and 17C) and graphs (FIGS. 17B and 17D) showing LPS or phage reduces the levels of phosphorylated Tie2 and ERK in HUVEC. HUVEC were serum-starved for 16 hours, then stimulated with LPS or phage for 10 minutes. Cells were lysed and the protein content was evaluated by Western Blot. Presented are Representative assays are presented showing that LPS and phages reduce levels of phosphorylated Tie2 (Y992) (FIGS. 17A and 17B) and Phospho-p44/42 MAPK (Erk1/2) (FIGS. 17C and 17D).

Phages and LPS Inhibit Endothelial Cells Activity and Vessels Sprouting

Figures 18A, 18B, 18C:
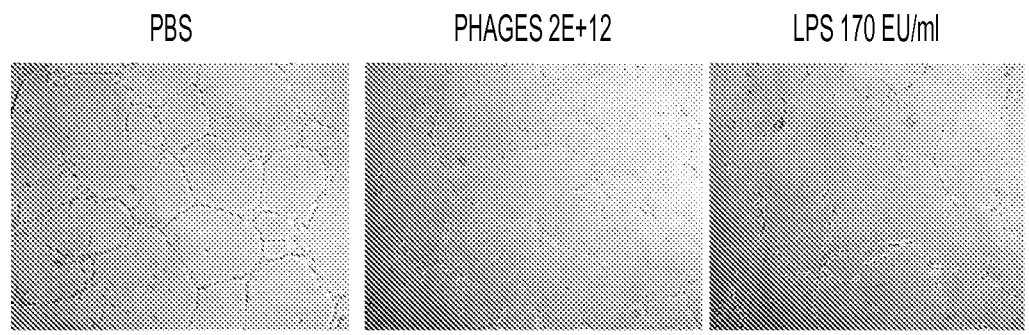
FIGS. 18A-18D are images (FIGS. 18A-18C) and a graph (FIG. 18D) showing that phage and LPS inhibit in vitro HUVEC tube formation.
Figure 18D:
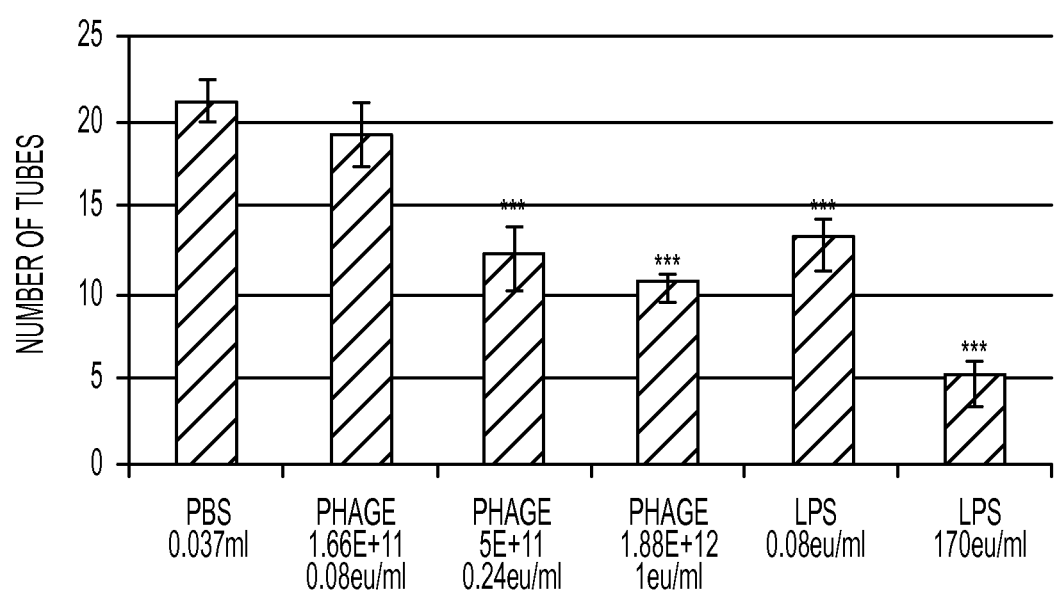

HUVEC were serum starved for 12 hours. Cells were suspended in EGM2 medium with the indicated samples and seeded in a matrigel coated 24 well plate. FIGS. 18A-18C are images and FIG. 18D is a graph showing that phage and LPS inhibit in vitro HUVEC tube formation. Results are presented as mean±SEM (***P<0.005 as compared to PBS)

FIGS. 19A-19E show the inhibition of in vitro angiogenesis by phage is dependent on LPS concentration in the phage preparation. HUVEC were serum starved for 12 hours. Cells were suspended in EGM2 medium with the indicated samples and seeded in a Matrigel coated 24 well plate. Results are presented as mean±SEM. (*P<0.05, ***P<0.005).

FIGS. 20A-20E show that LPS inhibits Ang1/Ang2 activity in in vitro HUVEC tube formation. HUVEC were serum-starved for 12 hours. Cells were suspended in EGM2 medium with the indicated samples and seeded in a matrigel coated 24 well plate. Tube length was quantified by measuring the length of capillary structures using software NIH ImageJ. Results are presented as mean±SEM (***P<0.005).

HUVEC ($5 \times 10^5$) were seeded in 6 well plate. Monolayer confluent cells were scratched to form a gap in the middle of the plate and images were taken. Wells were then supplemented with samples as indicated diluted in EGM2. After 13 hours, the plates were recorded and the number of cells invading the gap was counted using the ImageJ software. FIGS. 21A-21C show that LPS inhibits in vitro wound healing as significantly fewer cells in the gap area were visualized in wells supplemented with either TG1 bacteria supernatant or purified TG1 bacteria LPS compared with wells treated with PBS (*P<0.05).

Mice aorta rings (1 mm) were placed on matrigel and incubated with the indicated samples in EGM2 endothelial cells optimal media. FIGS. 22A-22D show that phage and LPS both significantly inhibited vessel sprouting in an aorta ring assay. Results are presented as mean±SEM (*P<0.05, **P<0.01 as compared to PBS).

Figure 23A:
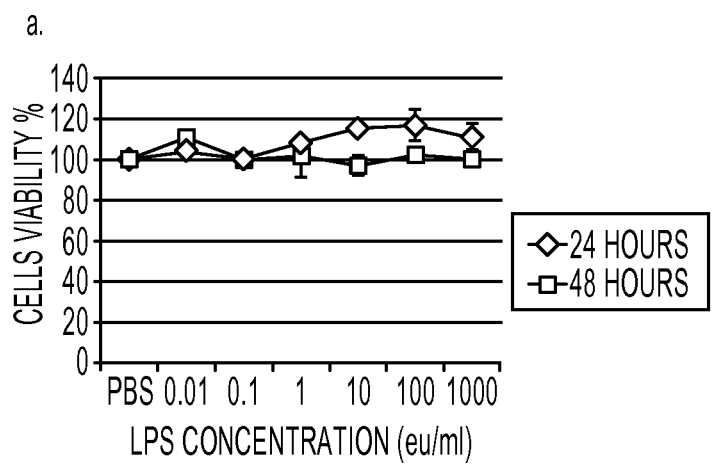
FIGS. 23A and 23B are graphs showing that the inhibition of endothelial cell activity is not mediated by cell toxicity caused by LPS or phage administration.
Figure 23B:
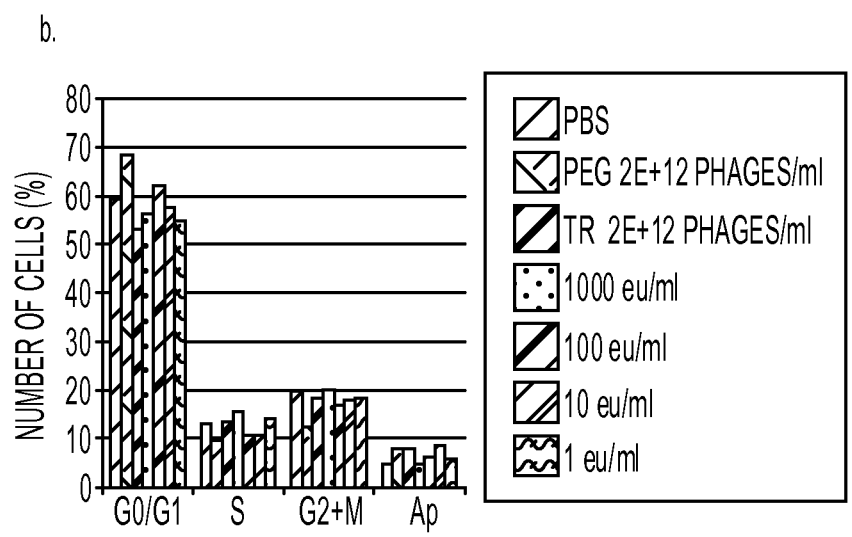

FIGS. 23A and 23B show that the inhibition of endothelial cell activity is not mediated by cell toxicity caused by LPS or phage administration. HUVEC were seeded in 96 well plates. At 50% confluence, wells were supplemented with the indicated LPS concentrations or PBS (FIG. 23A). Plates were incubated for 24 or 48 hours and cell viability was evaluated by the 3-(4,5-Dimethylthiazol-2-yl)-2,5-diphenyltetrazolium bromide (MTT) test. As demonstrated LPS did not induce decrease in cell viability. In FIG. 23B, HUVEC were seeded in 6 well plates and were supplemented with the indicated concentration of LPS or phages. 72 hours later, cells were subjected to cell cycle analysis by FACS. As shown, the percentage of cell death in all samples was below 10%.

Figure 24A:
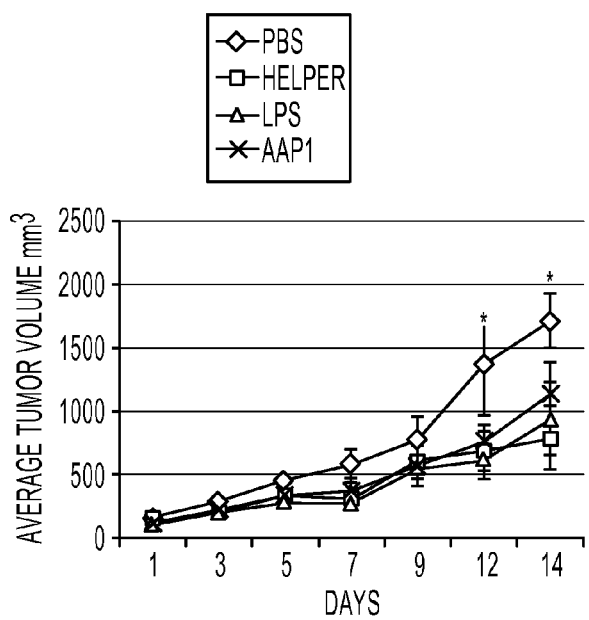
FIGS. 24A and 24B are graphs showing a similar trend of tumor inhibition between phage and LPS (FIG. 24A) with no significant change in body weight (FIG. 24B).
Figure 24B:
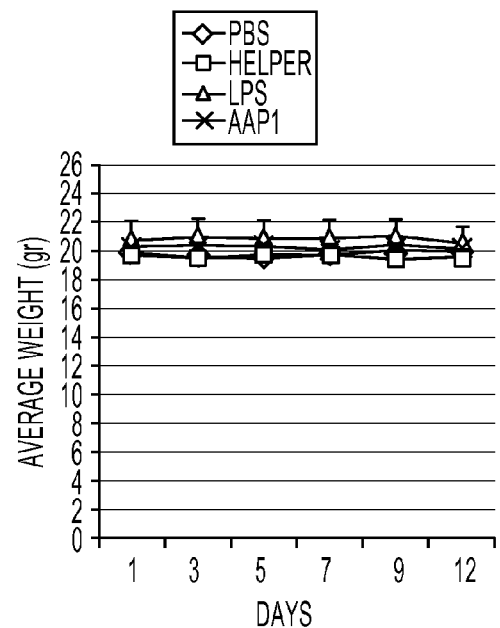
Figure 24C:
FIGS. 24C and 24D are an in vivo fluorescence image (FIG. 24C) and graph (FIG. 24D) showing correlation with tumor inhibition observed in FIG. 24A.
Figure 24D:
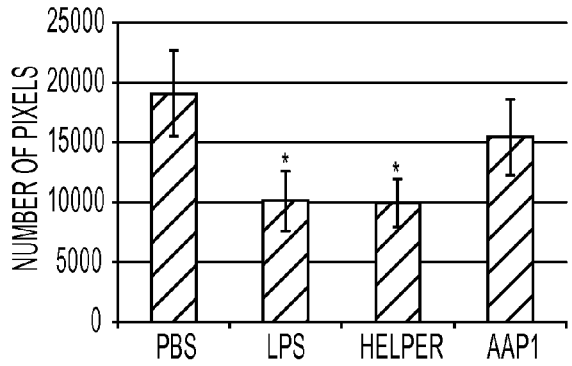
Figure 24E:
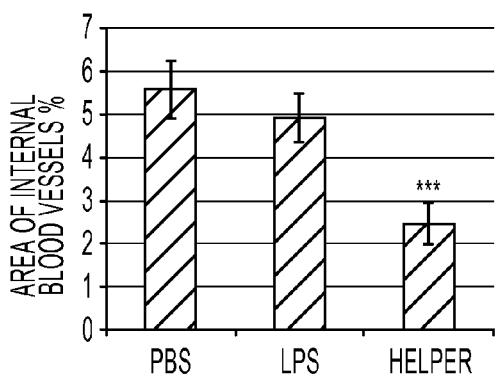
FIGS. 24E and 24F are a graph (FIG. 24E) and Doppler sonograph images (FIG. 24F) showing that phage decreases angiogenesis of internal blood vessels.
Figure 24F:
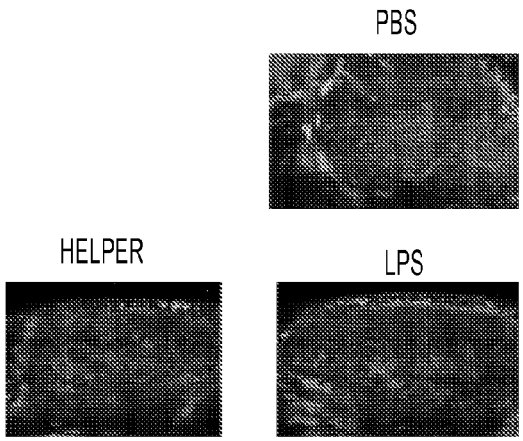
Figure 24H:
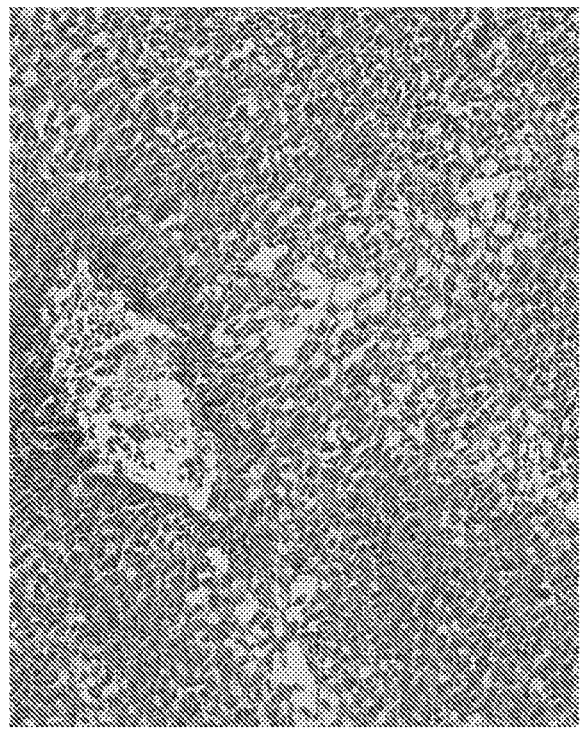
FIGS. 24G and 24H are images of histological analysis with H&E staining showing that phage decreases the number of blood vessels observed.
Figure 24G:
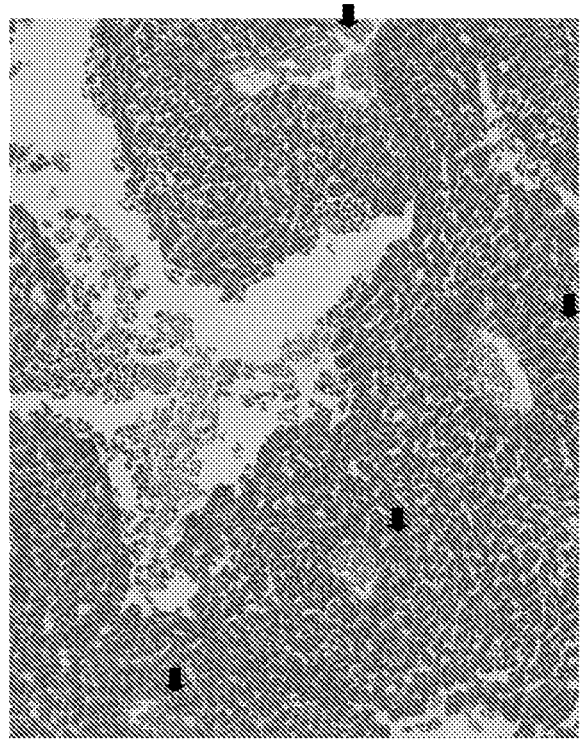

Both LPS and Phage Inhibit GBM Subcutaneous Tumor Growth and Angiogenesis In Vivo C57BL/6 female mice (n=5) were subcutaneously inoculated with 2E+6 GL261 murine GBM cells stably expressing GFP. Treatment started when tumors reached 110 mm$^3$. Mice received peritumoral injections in a total volume of 0.1 ml of either PBS, 1.7E+12 of Helper phage (430 endotoxin units per injection), 1.7E+12 of AAP1 (35 endotoxin units per injection) or LPS (430 endotoxin units per injection) on every second day. All phage and LPS were produced by the same bacteria (*E. coli* DH12S). LPS was purified by the LPS extraction kit (Intron) and phages were treated with triton to reduce endotoxin levels. Tumors dimensions were measured by a caliper and tumor volume was calculated as follows: width$^2$*length/2 The graph in FIG. 24A depicts similar trend of tumor inhibition between phage and LPS which was correlated to in vivo fluorescence readings (number of positive pixels) detected by the Maestro imaging instrument (FIGS. 24C and 24D) suggesting a role for LPS in phage anti-tumor activity. Both helper phage and LPS administration significantly inhibited tumor growth compared to the PBS control group. However, treatment with AAP1 which had lower endotoxin units concentration in this experiment was not able to significantly inhibit tumor growth thus further supporting dependence on LPS concentration. In FIGS. 24E and 24F, the effect of phage on tumor growth was accompanied by a significant decrease in angiogenesis of internal blood vessels as indicated by Doppler sonography. This observation was also supported by histopathology analysis with H&E staining (FIGS. 24G and 24H; arrows point to blood vessels). No significant change in body weight was observed during the experiment in the treated groups compared to the PBS control group (FIG. 24B; results are expressed as mean values±SEM, *P<0.05, ***P<0.005).

Figure 25A:
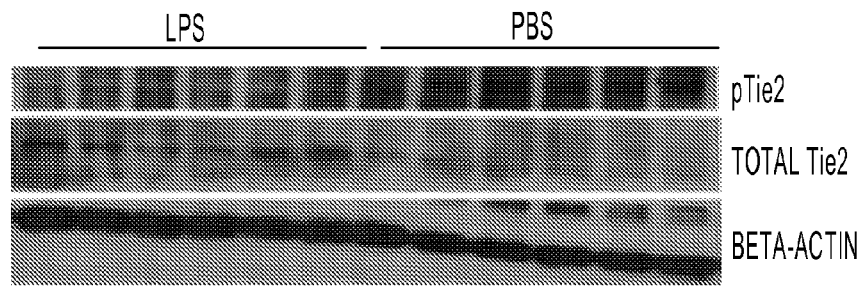
FIGS. 25A and 25D are Western blots and FIGS. 25B, 25C, 25E and 25F are graphs showing that treatment of subcutaneous tumors in mice with LPS downregulates Tie2 phosphorylation levels and downstream signaling.
Figure 25B:
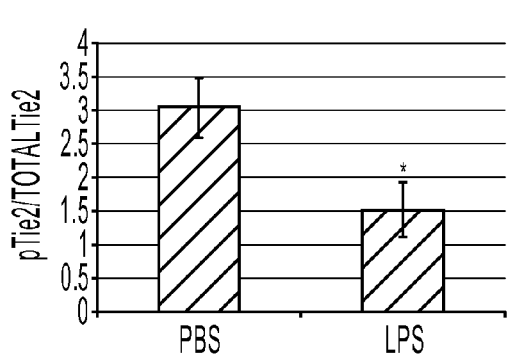
Figure 25C:
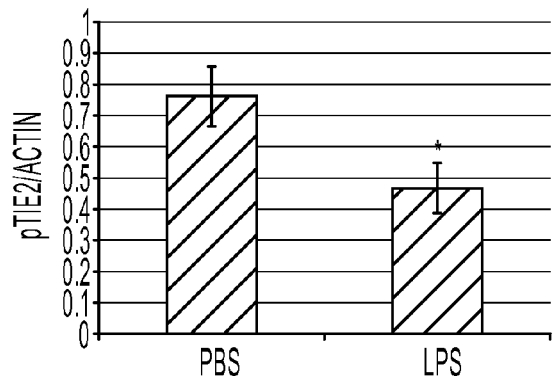
Figure 25D:
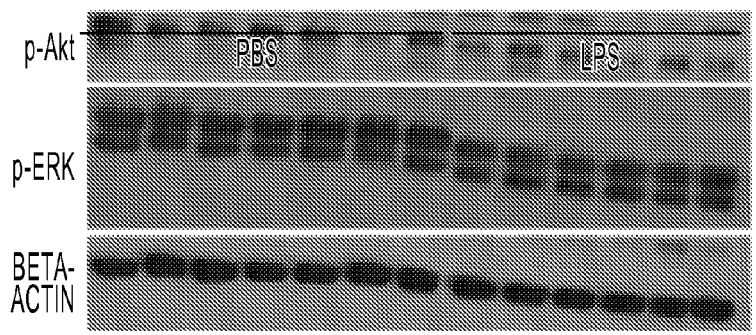
Figure 25E:
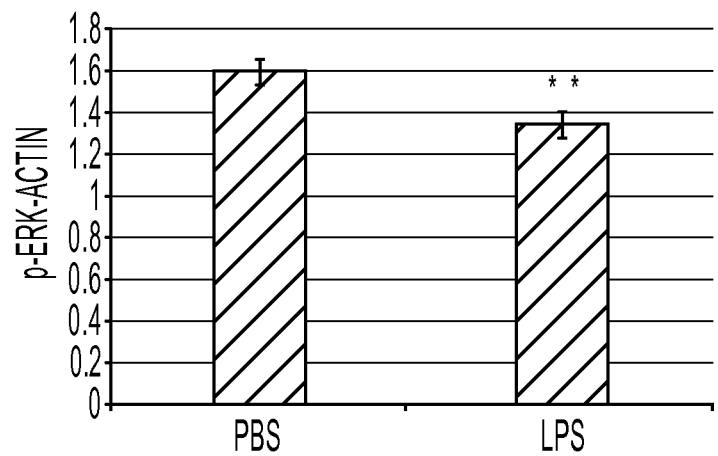
Figure 25F:
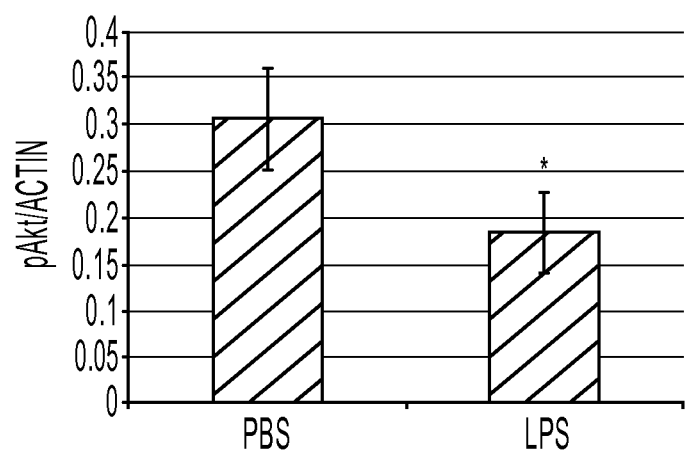

C57BL/6 female mice (n=6) were subcutaneously inoculated with 2E+6 GL261 murine GBM cells stably expressing GFP. Treatment started when the subcutaneous tumors reached 300 mm$^3$. Mice received peritumoral injection in a total volume of 0.1 ml of either PBS or LPS (450EU). After two hours, mice were perfused and tumors were collected. Tumors were homogenized in RIPA buffer supplemented with phosphatase and protease inhibitors. Protein content was analyzed in western blot with antibodies against phosphorylated Tie2 (Y992), total Tie2 (R&D), Phospho-p44/42 MAPK (Erk1/2, cell signaling), p-Akt (cell signaling) or beta-actin (FIGS. 25A and 25D). FIGS. 25B, 25C, 25E and 25F show a decrease in Tie2 phosphorylation as well as in Akt and ERK phosphorylation levels following treatment of tumors with LPS compared to control. Results are presented as mean±SEM (*P<0.05, **P<0.01).

Conclusions

The binding of Helper phage to rhTie2 was demonstrated to be specific and can be impaired by phage purification or by supplement of soluble LPS, suggesting that LPS mediates phages association with Tie2. It is also shown that phages can bind to Angiopoietin 2 (Ang2) which is a context dependent agonist/antagonist of Tie2, and is an important target in cancer therapy intervention (Huang et al., 2010). The localization of LPS on the surface of phages was confirmed and demonstrated that it is biologically active as indicated by immuno-purified phage reactivity in the LAL assay. Both phage and LPS can inhibit Tie2 signaling and affect ERK phosphorylation that controls angiogenesis and is found downstream to Tie2 (Huang et al., 2010; Brain et al., 1998; Meadows et al., 2001; and Shiojima et al., 2002). Phage and LPS can inhibit EC activity in vitro and vessel sprouting ex vivo. In the subcutaneous GBM allografts model, administration of LPS or phage with equal endotoxin units exhibited the same trend and both inhibited subcutaneous tumor progression in mice to the same extent. This highly suggests that LPS is the active agent in phage preparation and promotes their anti-tumor activity. This is also supported by the observation that in the same experiment the AAP1 preparation which contained lower LPS concentration compared to the helper phage preparation exhibited a moderate and non-significant anti-tumor activity unlike the helper phage that effectively inhibited tumor growth (The final concentration of LPS in each phage preparation varies even after applying the same purification technique). This can also explain our results from the previous section showing that helper phage had only moderate anti-tumor activity. In that experiment, helper phage but not AAP1 were purified by cesium in addition to TRITON and thus had lower endotoxin concentration compared to AAP1. However, it should be taken into consideration that AAP1 might have better anti-angiogenic and anti-tumorigenic activities than helper phages provided that both phages carry the same LPS amount (this was not tested in our experiments).

Notably, treatment with phage or LPS had no obvious side effect as indicated by mice average body weight which remained constant throughout the experiment. The anti-tumor activity of phage and LPS was accompanied by decrease in angiogenesis as demonstrated by Doppler sonography and was supported by histology analysis using H&E staining Administration of LPS to subcutaneous tumors in mice affects Tie2 signaling in vivo and downstream signaling such as p-ERK and p-Akt. The present inventors therefore conclude that phages are natural carriers of LPS which promotes their anti-angiogenic and anti-tumorigenic activities and their mechanism involves modulation of Tie2 signaling which is a key player in angiogenesis and cancer progression.

EXAMPLE 3

Bio-Distribution of Phages Following Intranasal Administration

Figure 26:
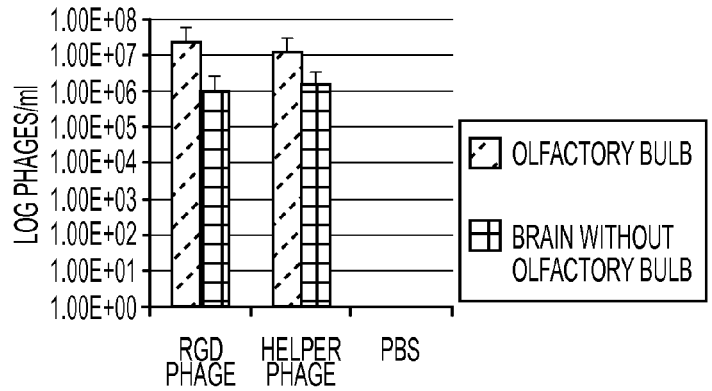
FIG. 26 is a graph showing phage concentration in mice olfactory bulb compared with the rest of brain.

Mice were intranasally administered with 2E+12 phages or PBS. After 1 hour mice were deeply anesthetized and perfused. Olfactory bulb was separated from the brain and both parts were homogenized and analyzed for phages concentration by live counting (n=3; FIG. 26).

Figure 27A:
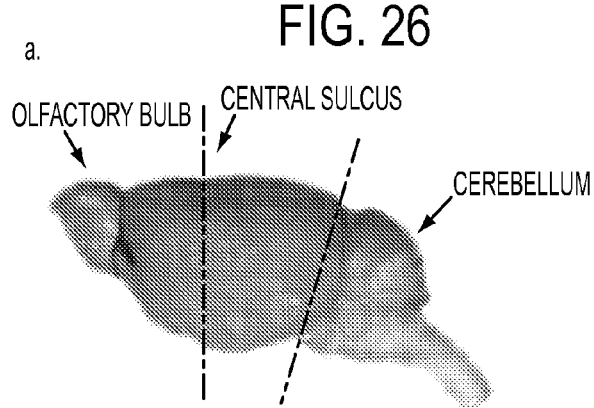
FIGS. 27A-27D are an image of mouse brain parts (FIG. 27A) and graphs (FIGS. 27B-27D) showing phage concentration in the anterior and posterior parts of the mouse brain and in different internal organs following intranasal administration.
Figure 27B:
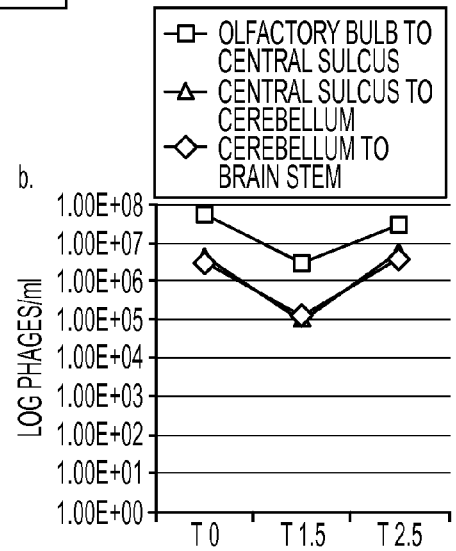
Figure 27C:
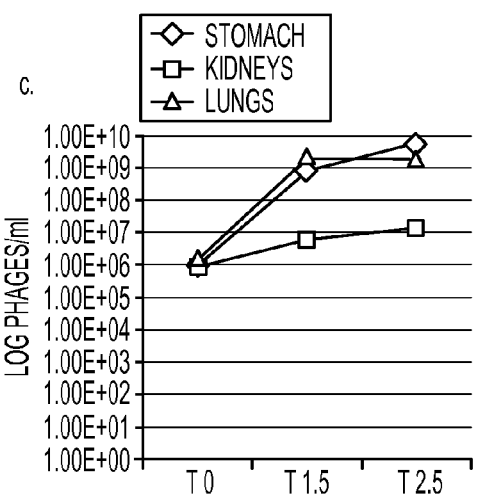
Figure 27D:
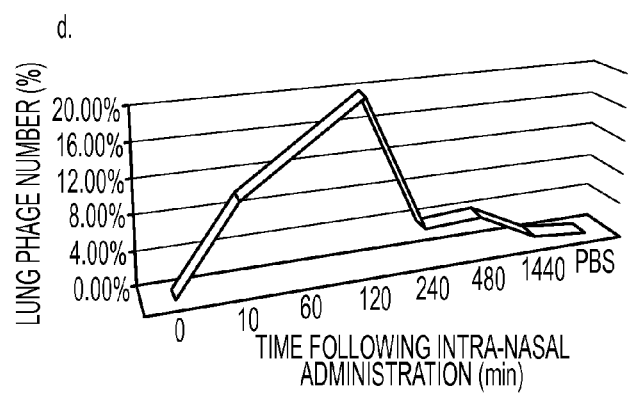

FIGS. 27D-27D show the phage concentration in the anterior and posterior parts of the mouse brain and in different internal organs following intranasal administration. Mice were intranasally administered with 2E+12 phages. At several time points, mice were deeply anesthetized and perfused. Different parts of mice brain (FIGS. 27A and 27B) and different internal organs (FIG. 27C) were evaluated for phages concentration by live counting. Clean aseptic operation tools were used for each brain part dissection (n=3). After two hours roughly 20% and 56% of the administered phage were recovered from the lungs and the stomach respectively. Phage concentration in the lungs peaks two hours following intranasal administration (FIG. 27D). Complete clearance is achieved after 24 hours.

Figure 28:
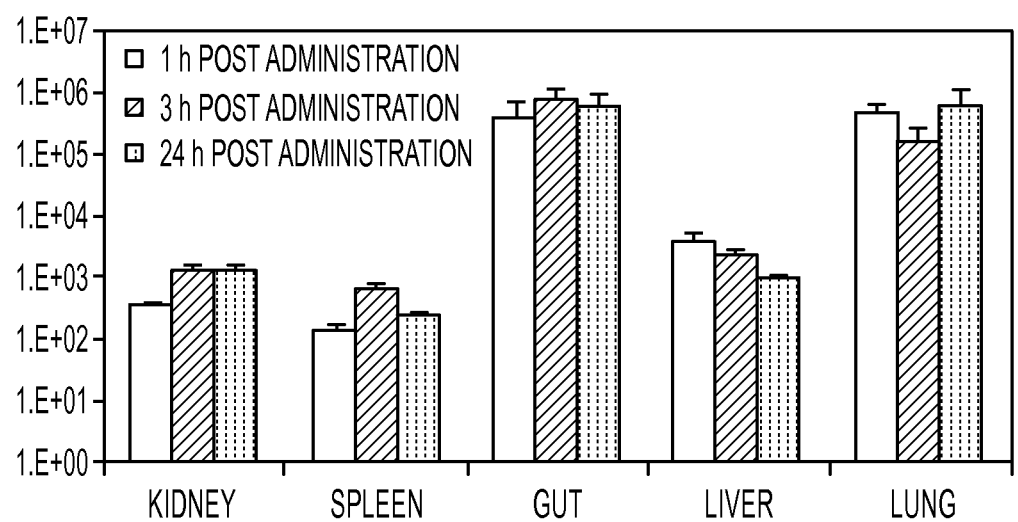
FIG. 28 is a graph showing phage localization in mice gut and other peripheral organs following intranasal administration.

BALB/C mice (n=3) were intranasally administered with 1.25E+12 helper phage labeled with 9 microcurie of $^{125}$I. Mice were perfused and sacrificed at different time points (1, 3, 24 hours) and gama radiation was evaluated in the indicated organs. FIG. 28 shows phage localization in mice gut and other peripheral organs following intranasal (IN) administration (Goren et al., 2007). Results are expressed in CPMs per organ weight (g) as well as mean±SD of each group.

Urine and feces were collected from mice that were administered IN with helper phage. Their excretions were analyzed for phages content several days following each administration by infecting *E. coli* cells with urine and feces samples and growing them on a kanamycin containing media (helper phages carry kanamycin resistance gene (M13KO7 Helper Phage, New England Biolabs)). The presence of phage in mice excretions was evaluated by sandwich ELISA with anti-phage polyclonal antibodies at the bottom and monoclonal antibodies on top. Phage was detected in urine and feces 3 weeks following IN administration. An additional examination, which was performed after 2 months, did not reveal phage in mice excretions.

FIGS. 29A-29D shows that intranasal administration of phage inhibits brain tumor growth and increases survival rate. A total of E+5 GL261 murine GBM cells were implanted into the thalamus of male C57BL/6 mice (n=6). Three days later, mice received intranasal administration of either PBS, 1.9E+12 triton purified Helper phages or purified LPS in a total volume of 0.02 ml (0.01 ml in each nostril) on every second day. Both Helper phages and LPS were produced in the same bacteria (*E. coli* DH12S). In both treatment groups, equal amount of endotoxin units (total of 975 eu) were given in each intranasal administration. At day 14 CT imaging was performed. Although both phages and LPS treatment inhibited tumor growth in mice brains, only phages administration resulted in a significant result (FIGS. 29A and 29B). A threshold of 10% decrease in mice weight from their initial weight at the day of cell inoculation was set to establish a Kaplan-Meier plot (FIG. 29C). Phages but not LPS increased survival rate by 33% in mice with GBM tumors compared to PBS control and reduced weight loss (n=8; FIG. 29C). This implies that phages pose an advantage over treatment with LPS alone in this model. Results are expressed as mean values±SEM, *P<0.05.

Figure 30:
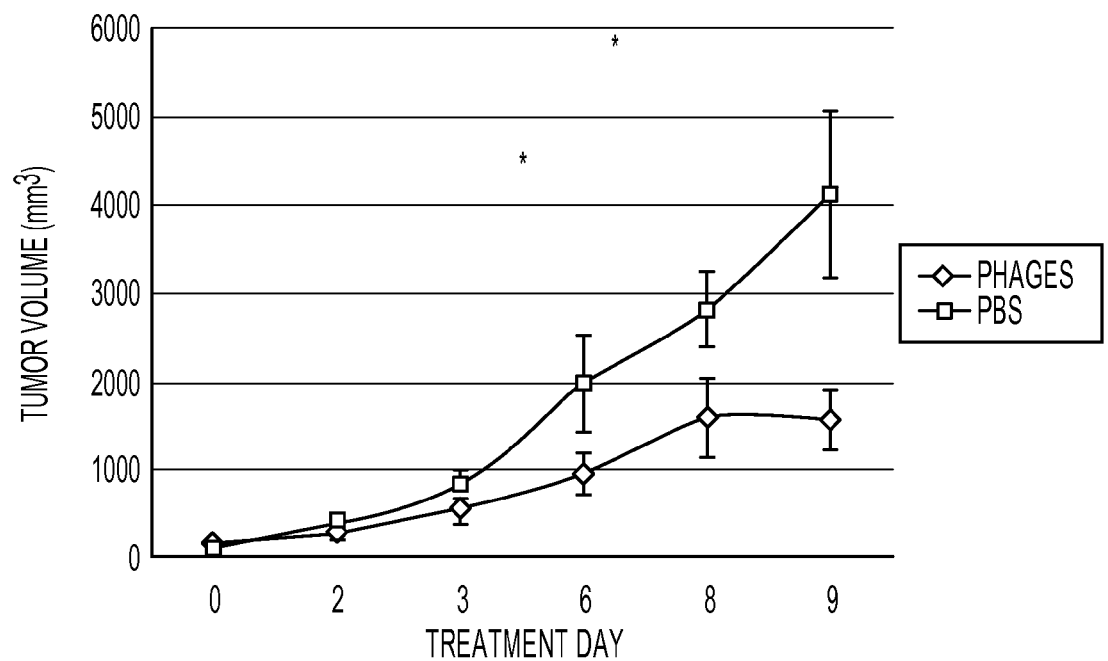
FIG. 30 is a graph showing that peritumoral administration of phage inhibits Lewis lung carcinoma (LLC) subcutaneous tumors.

C57BL/6 male mice (10 w/o) were inoculated subcutaneously in the flank with E+6 LLC cells in a total volume of 0.1 ml. Treatment started when tumors reached 100 mm$^3$. Mice received peritumoral injections every second day of either PBS or 1.8E+12 triton purified phages. Tumors growth and volume was monitored with a caliper as described above. FIG. 30 shows that peritumoral administration of phages inhibits Lewis lung carcinoma (LLC) subcutaneous tumors. Results are expressed as mean values±SEM (*P<0.05).

Figure 31A:
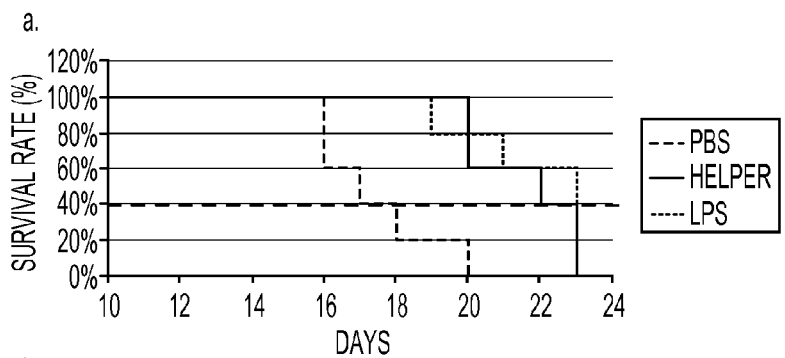
FIGS. 31A-31E are a Kaplan-Meier plot (FIG. 31A), graphs (FIGS. 31B and 31C), visible light/fluorescence imaging (FIG. 31D) and CT imaging (FIG. 31E) showing that intranasal administration of phage or LPS inhibits lung tumor growth and increases survival rate in mice.
Figure 31B:
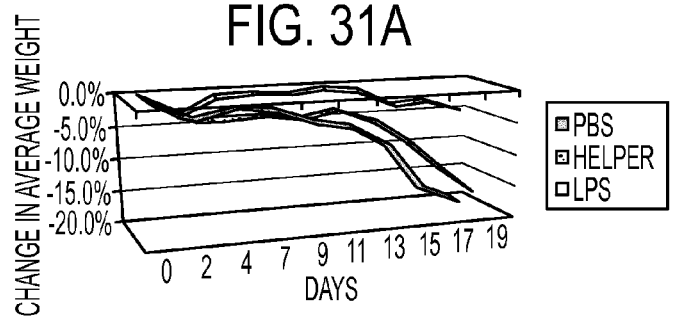
Figure 31C:
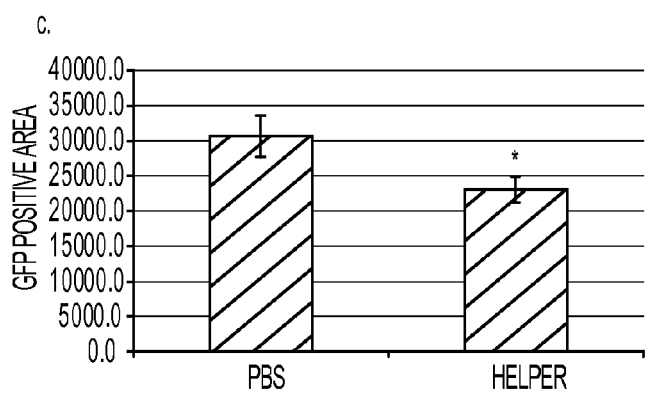
Figure 31D:
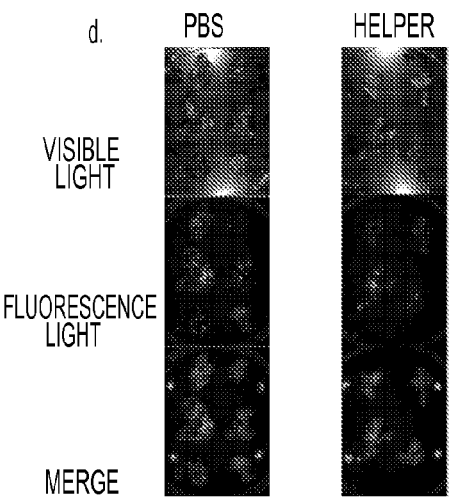
Figure 31E:
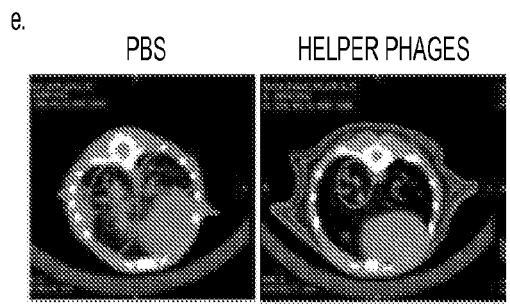
Figure 33A:
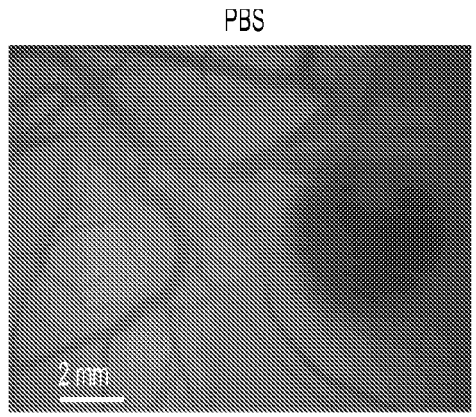
FIGS. 33A-33C are images and FIG. 33D is a graph showing that helper phage and AAP1 promote blood vessel formation in chick chorioallantoic membrane.
Figure 33B:
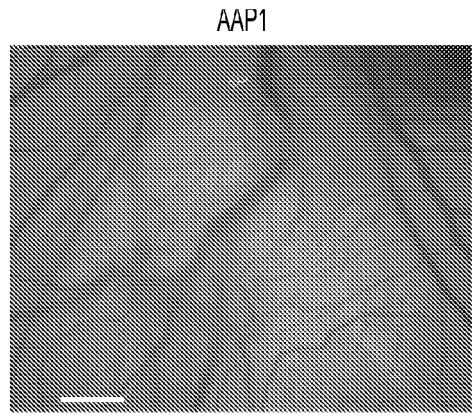
Figure 33C:
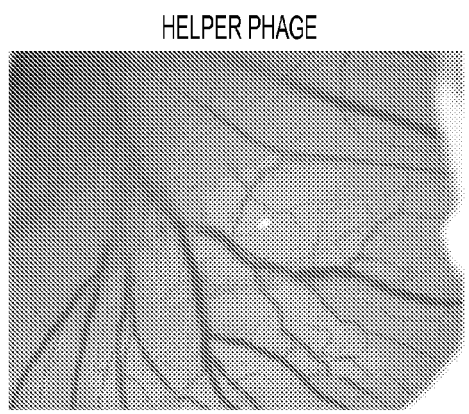
Figure 33D:
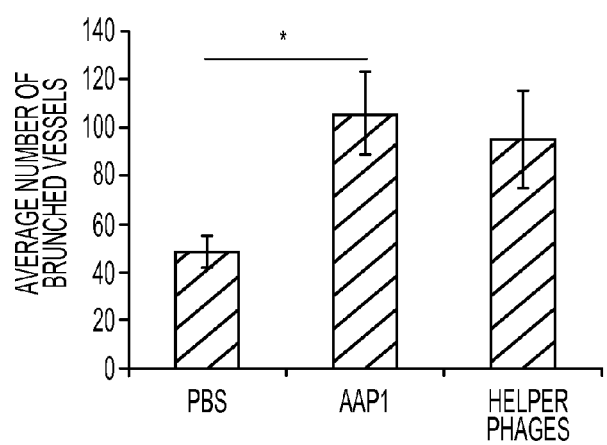

FIGS. 31A-31E show that intranasal administration of phage or LPS inhibits lung tumor growth and increases the survival rate in mice. C57BL/6 male mice (9-13 w/o, n=5) were inoculated intravenously via the tail vein with E+6 LLC stably expressing GFP. Treatment started 7 days after cells inoculation. Mice received intranasal administration of either PBS, 4.4E+11 Helper phage or equal amount of endotoxin units in a total volume of 0.02 ml (0.01 ml in each nostril) every second day. Both LPS and Helper phages were produced in the same bacteria (*E. coli* DH12S). A threshold of 10% decrease in mice weight from their initial weight at the day of cells inoculation was set to establish a Kaplan-Meier plot (FIG. 31A). Treatment of mice with either LPS or phages improved survival rate by approximately 30%. Both LPS or phages administration inhibited mice weight loss compared to PBS control with a clear advantage of LPS treatment over phages administration (FIG. 31B). Intranasal administration of phages to mice with lung tumors (n=5, LLC-GFP tumors) results in inhibition of tumor growth as indicated by reduction in fluorescence readings in ex-vivo lungs imaging by the Maestro instrument (FIGS. 31C and 31D). Reduction in tumor growth was also supported by in vivo CT imaging (FIG. 31E). Results are expressed as mean values±SEM (*P<0.05).

Conclusions

Live counting from mice brain homogenates shows rapid penetration of phage to the CNS following IN administration. The highest concentration of phage was found in the region of the olfactory bulb minutes following IN administration indicating that phages use an extracellular transport via the olfactory system to gain access to the brain (intracellular transport takes hours to days; Chapman et al., 2012).

However localization of phages both in anterior and posterior regions of the brain shortly following IN administration suggests that an alternative pathway might be involved. The present inventors propose that phage also use an extracellular transport via the trigeminal nerve which connects to the pons and the cribriform plate and therefore facilitates transport to both anterior and posterior regions of the brain following IN administration (Chapman et al., 2012). In addition, phage might use other pathways to reach the CNS such as an intracellular pathway through the olfactory and the trigeminal nerves or transport via the blood circulation.

The present inventors also found that approximately 20% of the IN administered phages are inhaled and are found in the lungs. The present inventors then show that peritumoral administration of phages inhibited subcutaneous tumor development of Lewis lung carcinoma (LLC) cells which prompted evaluation of phage efficacy in inhibiting LLC tumors in the lungs. This also demonstrates that phage anti-tumor activity is not restricted to GBM tumors and that that phage mechanism can be utilized to effectively inhibit other solid tumors growth. The present inventors also show that IN administration of phages can significantly inhibit orthotopic lung tumor progression and this activity was also accompanied by increase in mice survival rate. The present inventor further found that IN administration of soluble LPS without phage increased mice survival rate and inhibited mice weight loss in that experiment. This further supports the observation that LPS promotes phage anti-tumor activity. However both anti- and pro-tumorigenic activities of LPS are described in the scientific literature (Melkamu et al., 2013; Chicoine et al., 2007; Moriya et al., 1984; and Dabrowska et al., 2004). This is in line with a recent report showing that IN administration of LPS increases lung tumor progression (Melkamu et al., 2013). The nature of LPS contradictive activity in tumorigenesis is not fully understood; however, it should be taken into consideration that different LPS serotypes can exert different activities when they are introduced to mammalian cells (Bryant et al., 2010). Here, the present inventors demonstrate that soluble LPS or phage LPS complexes that origin from *E. coli* DH12S bacteria have anti-tumorigenic activities (LPS structure varies between bacteria).

In a murine GBM orthotopic model, IN administration of phage significantly inhibited tumor progression and increased mice survival rate. However, in this model, phage anti-tumor activity was superior to the anti-tumor activity of LPS. A possible explanation is that LPS forms micelles in aqueous solutions (Anspach, 2001; Gorbet et al., 2005; and Darkow et al., 1999) that might impair its ability to penetrate to the CNS. This is supported by the observation that phage that acquired spheroid structure following treatment with chloroform were not able to reach the brain following IN administration (Frenk et al., 2002). Therefore, in a brain tumor model, IN administration of phages facilitate LPS delivery to the brain and pose an advantage over treatment with soluble LPS.

In addition, the present inventors found that most of the IN administered phage accumulate in the stomach (56%). These phage survived the extreme conditions of the stomach and remained intact as their infectivity was not impaired. Furthermore, the laboratory of the present inventors had previously shown that phage can be isolated from mice gut and stool samples (Goren et al., 2007) indicating that phage pass through the upper and lower digestive tracts following IN administration. This implies that IN or oral administration of phage might be utilized in inhibiting gastrointestinal (GI) cancers that are the most deadly and most common cancers worldwide following lung cancer (Ferlay et al., 2010; and who.int/mediacentre/factsheets/).

EXAMPLE 4

Phages and LPS can Promote Angiogenesis in Some Settings

HUVEC were incubated with TRITON purified helper phage, AAP1 or wild type phage (E+12) for 30 min. Cells were then seeded on fibronectin coated 96 wells, and left to adhere for 45 minutes. Wells were washed, fixed with Paraformaldehyde (PFA) 4% and stained with crystal violet. Cells treated with AAP1, wild type filamentous phage or helper filamentous phage exhibited enhanced adhesion to fibronectin compared with untreated cells (FIGS. 32A-32F). Results are expressed as mean values±SEM (*$P<0.05$ as compared to untreated cells).

PEG purified Helper phage or AAP1 (2E+12) were administered to the chick chorioallantoic membrane (CAM) on day 7 of embryo development (E7) through a shell window. The window was sealed and eggs were incubated for 48 hours at 37° C. Images of the CAM were taken and blood vessels were counted. FIGS. 33A-33D show that the number of blood vessels was significantly elevated in phage treated CAM compared with PBS control ($p<0.05$) and that helper phage and AAP1 promote blood vessels formation in vivo.

Conclusion

The pro-angiogenic activity of LPS is well documented in the scientific literature (Pollet et al., 2003; and Mattsby-Baltzer et al., 1994). The present inventors demonstrate here that phages as carriers of LPS also acquire pro-angiogenic activities in some settings. This means that phages have a context dependent activity and can promote vessel formation in some environments and inhibit angiogenesis in others. Although phages show anti-angiogenic activities in the context of tumorigenesis, they might induce pro-angiogenic activities in other pathologies when the right conditions are provided. This is supported by the association of phage and LPS with Tie2 which is well known for the context dependent nature of its ligands. For example, the activity of Ang1 can be either anti- or pro-angiogenic depending on whether it acts in the context of quiescent or non-resting vasculature, respectively (Thurston et al., 2000; Sharinen et al., 2008; Fukuhara et al., 2008; Fukuhara et al., 2009; and Huang et al., 2010). Ang2 activity is also context dependent as it can either promote vessel sprouting or lead to vessel regression depending on its concentration and the presence of other growth factors such as VEGF and Ang1 (Huang et al., 2010; Kim et al., 2000; Cao et al., 2007; Lobov et al., 2002; Hashizume et al., 2010; and Yuan et al., 2009). The activity of Ang2 is in particular intriguing because it competes with Ang1 over the same binding site in Tie2 and while both ligands have the same affinity (Maisonpierre et al., 1997; Barton et al., 2006; and Fiedler et al., 2003) Ang2 generally does not induce receptor phosphorylation and therefore antagonizes Ang1 activity (Maisonpierre et al., 1997; and Reiss et al., 2007). The nature of this activity was suggested to emanate from the extent of the ligand oligomerization as COMP-Ang2, a higher-order oligomerized form of Ang2 can induce Tie2 phosphorylation and imparts agonistic activity (Kim et al., 2009). Furthermore non-genetically manipulated Ang2 was demonstrated to induce Tie2 phosphorylation in some conditions yet the exact mechanism for its context dependent activity is unknown (Kim et al., 2000; Teichert-Kuliszewska et al., 2001; and Daly et al., 2006).

Therefore, Tie2 phosphorylation and activation can lead to contradictive outcomes in angiogenesis and the same ligand can either serve as an agonist or antagonist of Tie2 depending on its association with other ligand monomers or the presence of other factors. Interestingly, LPS monomers with their size varied according to their oligosaccharide chain can also associate to form supramolecular structures in aqueous solutions with a molecular weight range of 10 kDa to more than 1000 kDa (Anspach, 2001; Gorbet et al., 2005; and Darkow et al., 1999). Whether some of these structures are recognized by Tie2 and can therefore modulate its activation needs further investigation. However, this hypothesis can further explain LPS and phage context dependent activity.

As mentioned earlier, phage can introduce LPS to the CNS following IN administration better than IN administration of LPS alone. Provided the right conditions, this might lead to angiogenesis and can be proven beneficial in the treatment of pathologies where angiogenesis is impaired or required such as ischemia (Ferraral et al., 2005) or neurodegenerative diseases (Wang et al., 2011) that have a distinct and different profile than tumorigenesis.

Final Conclusions and Significance

Phage with a wild type-like phenotype (helper phage) can affect endothelial cells (EC) activity and angiogenesis in vitro and in vivo and inhibit tumor progression Inhibition of EC activity is not due to cell toxicity and might be attributed to phage ability to interfere with the Tie2/Ang system which has a crucial role in angiogenesis. The effect of phage on Tie2, EC activity, angiogenesis and tumor growth is at least partially mediated by LPS, which the present inventors show that is attached to the filamentous phage and inhibits EC activity. The present inventors then demonstrate that both LPS and phage inhibit subcutaneous allografts to the same extent following peritumoral administration. Intranasal (IN) administration of phage was shown to result in their biodistribution in the brain and lungs and phage was shown to significantly inhibit orthotopic brain and lungs tumor growth and increase mice survival rate following IN administration. In these models, soluble LPS also exhibited anti-tumorigenic activity following IN administration. However, the results show that phage has an advantage over soluble LPS in inhibiting brain tumors progression following IN administration plausibly due to better penetration properties to the CNS.

The present inventors demonstrate that phage pass throughout the GI and accumulate in mice gut including the stomach and were also found in mice feces which points to a potential use of phage in treating GI cancers. The present inventors also demonstrate that phage can have pro-angiogenic activities in some settings and that can be utilized in treating pathologies such as ischemia where angiogenesis can improve the course of the disease.

The present inventors' discovery shows that filamentous phages are not neutral to the mammalian host, and can interfere with endothelial cells activity and angiogenesis. This can be utilized to treat angiogenesis-related pathologies. In particular, phage are useful in treating brain pathologies due to their unique ability to penetrate the CNS. This work also demonstrates that LPS is not merely angiogenic but can also exert anti-angiogenic activities and inhibit tumor progression following IN administration. The involvement of angiogenesis in a wide range of pathologies including cancer, inflammatory and neurodegenerative diseases implies that angiogenesis modulators such as filamentous phages and LPS might be useful in a large variety of applications.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Adamson C, Kanu O O, Mehta A I, Di C, Lin N, Mattox A K, Bigner D D. Glioblastoma multiforme: a review of where we have been and where we are going. *Expert Opin Investig Drugs.* 2009 August; 18(8):1061-83.

Anspach F B. Endotoxin removal by affinity sorbents. *J Biochem Biophys Methods.* 2001 Oct. 30; 49(1-3):665-81

Anton K, Baehring J M, Mayer T. Glioblastoma multiforme: overview of current treatment and future perspectives. *Hematol Oncol Clin North Am.* 2012 August; 26(4):825-53.

Aota S, Nomizu M, Yamada K M. The short amino acid sequence Pro-His-Ser-Arg-Asn in human fibronectin enhances cell-adhesive function. *J Biol Chem.* 1994 Oct. 7; 269(40):24756-61.

Ausman J I, Shapiro W R, Rall D P. Studies on the chemotherapy of experimental brain tumors: development of an experimental model. *Cancer Res.* 1970 September; 30(9):2394-400.

Barton W A, Tzvetkova-Robev D, Miranda E P, Kolev M V, Rajashankar K R, Himanen J P, Nikolov D B. Crystal structures of the Tie2 receptor ectodomain and the angiopoietin-2-Tie2 complex. *Nat Struct Mol Biol.* 2006 June; 13(6):524-32.

Beat A Imhof & Michel Aurrand-Lions (2006) Angiogenesis and inflammation face off Nature *Medicine*—12, 171-172

Brian P. Eliceiri, Richard Klemke, Staffan Stromblad, and David A. Cheresh. Integrin αvβ3 Requirement for Sustained Mitogen-activated Protein Kinase Activity during Angiogenesis. *J Cell Biol.* 1998 Mar. 9; 140(5): 1255-1263.

Bryant C E, Spring D R, Gangloff M, Gay N J. The molecular basis of the host response to lipopolysaccharide. *Nat Rev Microbiol.* 2010 January; 8(1):8-14.

Cao Y, Sonveaux P, Liu S, Zhao Y, Mi J, Clary B M, Li C Y, Kontos C D, Dewhirst M W. Systemic overexpression of angiopoietin-2 promotes tumor microvessel regression and inhibits angiogenesis and tumor growth. *Cancer Res.* 2007 April Carmeliet P. Angiogenesis in life, disease and medicine. Nature 438:932-936 (2005).

Chapman C D, Frey W H 2nd, Craft S, Danielyan L, Hallschmid M, Schioth H B, Benedict C. Intranasal Treatment of Central Nervous System Dysfunction in Humans. *Pharm Res.* 2012 Nov. 8.

Chicoine M R, Zahner M, Won E K, Kalra R R, Kitamura T, Perry A, Higashikubo R. The in vivo antitumoral effects of lipopolysaccharide against glioblastoma multiforme are mediated in part by Toll-like receptor 4. *Neurosurgery.* 2007 February; 60(2):372-80

Crawford T N, Alfaro D V 3rd, Kerrison J B, Jablon E P. Diabetic retinopathy and angiogenesis. *Curr Diabetes Rev.* 2009 February; 5(1):8-13.

D. Creamer, D. Sullivan, R. Bicknell & J. Barker (2003) Angiogenesis in psoriasis. *Angiogenesis* 5: 231-236

Dabrowska K, Opolski A, Wietrzyk J, Switala-Jelen K, Godlewska J, Boratynski J, Syper D, Weber-Dabrowska B, Gorski A. Anticancer activity of bacteriophage T4 and its mutant HAP1 in mouse experimental tumour models. *Anticancer Res.* 2004 November-December; 24(6):3991-5.

Christopher Daly, Elizabeth Pasnikowski, Elena Burova, Vivian Wong, Thomas H. Aldrich, Jennifer Griffiths, Ella Ioffe, Thomas J. Daly, James P. Fandl, Nick Papadopoulos, Donald M. McDonald, Gavin Thurston, George D. Yancopoulos, and John S. Rudge. Angiopoietin-2 functions as an autocrine protective factor in stressed endothelial cells. *Proc Natl Acad Sci USA.* 2006 Oct. 17; 103(42): 15491-15496.

Darkow R, Groth T, Albrecht W, Lützow K, Paul D. Functionalized nanoparticles for endotoxin binding in aqueous solutions. *Biomaterials.* 1999 Jul.; 20(14):1277-83.

Dvorak H F. Angiogenesis: update (2005) *J Thromb Haemost.* 3(8):1835-42.

Eriksson et al., (2007) Tumor specific phage particles promote tumor regression in a mouse melanoma model. *Cancer Immunol Immunother.*; 56:677-687.

Eriksson et al., (2009) Tumor-specific bacteriophages induce tumor destruction through activation of tumor-associated macrophages. *The Journal of Immunology;* 3105-3111.

Ferlay J, Shin H R, Bray F, Forman D, Mathers C, Parkin D M. Estimates of worldwide burden of cancer in 2008: GLOBOCAN 2008. *Int J Cancer.* 2010 Dec. 15; 127(12): 2893-917

Napoleone Ferraral, Robert S. Kerbel (2005) Angiogenesis as a therapeutic target. *Nature* 438, 967-974

Fiedler U, Krissl T, Koidl S, Weiss C, Koblizek T, Deutsch U, Martiny-Baron G, Marmé D, Augustin H G. Angiopoietin-1 and angiopoietin-2 share the same binding domains in the Tie-2 receptor involving the first Ig-like loop and the epidermal growth factor-like repeats. *J Biol Chem.* 2003 Jan. 17; 278(3)

Frenkel D, Solomon B. Filamentous phage as vector-mediated antibody delivery to the brain. *Proc Natl Acad Sci USA.* 2002 Apr. 16; 99(8):5675-9

Fukuhara S, Sako K, Minami T, Noda K, Kim H Z, Kodama T, Shibuya M, Takakura N, Koh G Y, Mochizuki N. Differential function of Tie2 at cell-cell contacts and cell-substratum contacts regulated by angiopoietin-1. *Nat Cell Biol.* 2008 May; 10(5):513-26.

Shigetomo Fukuhara, Keisuke Sako, Kazuomi Noda, Kaori Nagao, Koichi Miura, and Naoki Mochizuki. Tie2 is tied at the cell-cell contacts and to extracellular matrix by Angiopoietin-1. *Exp Mol Med.* 2009 Mar. 31; 41(3): 133-139.

Ghassan K. Abou-Alfa, M D; Philip Johnson, M D; Jennifer J. Knox, M D; Marinela Capanu, PhD; Irina Davidenko, M D; Juan Lacava, M D; Thomas Leung, M D; Bolorsukh Gansukh, B S; Leonard B. Saltz, M D (2010) Doxorubicin Plus Sorafenib vs Doxorubicin Alone in Patients With Advanced Hepatocellular Carcinoma. *JAMA.* 304(19): 2154-2160.

Gorbet M B, Sefton M V. Endotoxin: the uninvited guest. *Biomaterials.* 2005 December; 26(34):6811-7.

Goren. O. Solomon B. Phage therapy against Alzheimer disease. PhD thesis, department of molecular microbiology and biotechnology, Tel-Aviv university 2007

Hashizume H, Falcón B L, Kuroda T, Baluk P, Coxon A, Yu D, Bready J V, Oliner J D, McDonald D M. Complementary actions of inhibitors of angiopoietin-2 and VEGF on tumor angiogenesis and growth. *Cancer Res.* 2010 Mar. 15; 70(6):2213-23.

Hosoi T, Tamubo T, Horie N, Okuma Y, Nomura Y, Ozawa K. (2010) TEK/Tie2 is a novel gene involved in endoplasmic reticulum stress. *J Pharmacol Sci.* 114(2):230-3.

Huang H, Bhat A, Woodnutt G, Lappe R. Targeting the ANGPT-TIE2 pathway in malignancy. *Nat Rev Cancer.* 2010 August; 10(8):575-85

Hurwitz, H., Fehrenbacher, L., Novotny, W., Cartwright, T., Hainsworth, J., Heim, W., et al., (2004) Bevacizumab plus irinotecan, fluorouracil, and leucovorin for metastatic colorectal cancer. *New Engl. J. Med.* 350, 2335-2342.

Kim H Z, Jung K, Kim H M, Cheng Y, Koh G Y. A designed angiopoietin-2 variant, pentameric COMP-Ang2, strongly activates Tie2 receptor and stimulates angiogenesis. *Biochim Biophys Acta.* 2009 May; 1793(5):772-80

Kim I, Kim J H, Moon S O, Kwak H J, Kim N G, Koh G Y. Angiopoietin-2 at high concentration can enhance endothelial cell survival through the phosphatidylinositol 3'-kinase/Akt signal transduction pathway. *Oncogene.* 2000 Sep. 14; 19(39):4549-52.

Robert S. Kerbel (2008) Tumor angiogenesis. *N Engl J Med* 358:2039-2049

Lobov I B, Brooks P C, Lang R A. Angiopoietin-2 displays VEGF-dependent modulation of capillary structure and endothelial cell survival in vivo. *Proc Natl Acad Sci USA.* 2002 Aug. 20; 99(17):11205-10

Maas J W, Groothuis P G, Dunselman G A, de Goeij A F, Struyker Boudier H A, Evers J L (2001) Endometrial angiogenesis throughout the human menstrual cycle. *Hum. Reprod.* 16 (8): 1557-1561.

Maisonpierre P C, Suri C, Jones P F, Bartunkova S, Wiegand S J, Radziejewski C, Compton D, McClain J, Aldrich T H, Papadopoulos N, Daly T J, Davis S, Sato T N, Yancopoulos G D. Angiopoietin-2, a natural antagonist for Tie2 that disrupts in vivo angiogenesis. *Science.* 1997 Jul. 4; 277(5322):55-60.

Matijs van Meurs, Philipp Kiimpers, Jack J M Ligtenberg, John H J M Meertens, Grietje Molema and Jan G Zijlstra. (2009) Bench-to-bedside review: Angiopoietin signalling in critical illness—a future target? *Critical Care,* 13:207.

Mattsby-Baltzer I, Jakobsson A, Sörbo J, Norrby K. Endotoxin is angiogenic. Int J Exp Pathol. 1994 June; 75(3): 191-6.

Meadows K N, Bryant P, Pumiglia K. Vascular endothelial growth factor induction of the angiogenic phenotype requires Ras activation. *J Biol Chem.* 2001 Dec. 28; 276(52):49289-98.

Melkamu T, Qian X, Upadhyaya P, O'Sullivan M G, Kassie F. Lipopolysaccharide Enhances Mouse Lung Tumorigenesis: A Model for Inflammation-Driven Lung Cancer. *Vet Pathol.* 2013 Feb. 4

Moriya N, Miwa H, Orita K. Antitumor effects of bacterial lipopolysaccharide and tumor necrosis factor in mice. Jpn J Surg. 1984 March; 14(2):163-6.

Moulton K S. Plaque angiogenesis and atherosclerosis. *Curr Atheroscler Rep.* 2001 May; 3(3):225-33.

Palmieri D, Chambers A F, Felding-Habermann B, Huang S, Steeg P S. The biology of metastasis to a sanctuary site. *Clin Cancer Res.* 2007 Mar. 15; 13(6):1656-62.

Pollet I, Opina C J, Zimmerman C, Leong K G, Wong F, Karsan A. Bacterial lipopolysaccharide directly induces angiogenesis through TRAF6-mediated activation of NF-kappaB and c-Jun N-terminal kinase. *Blood.* 2003 Sep. 1; 102(5):1740-2

Rakonjac J, Bennett N J, Spagnuolo J, Gagic D, Russel M. Filamentous bacteriophage: biology, phage display and nanotechnology applications. *Curr Issues Mol Biol.* 2011; 13(2):51-76.

Reiss Y, Droste J, Heil M, Tribulova S, Schmidt M H, Schaper W, Dumont D J, Plate K H. Angiopoietin-2 impairs revascularization after limb ischemia. *Circ Res.* 2007 Jul. 6; 101(1):88-96.

Risau W (1997) Mechanisms of angiogenesis. *Nature.* 17; 386(6626):671-4.

Saharinen P, Eklund L, Miettinen J, Wirkkala R, Anisimov A, Winderlich M, Nottebaum A, Vestweber D, Deutsch U, Koh G Y, Olsen B R, Alitalo K. Angiopoietins assemble distinct Tie2 signalling complexes in endothelial cell-cell and cell-matrix contacts. *Nat Cell Biol.* 2008 May; 10(5): 527-37

Shiojima I, Walsh K. Role of Akt signaling in vascular homeostasis and angiogenesis. Circ Res. 2002 Jun. 28; 90(12):1243-50.

Sunitinib malate for metastatic castration-resistant prostate cancer following docetaxel-based chemotherapy *Ann Oncol* (2010) 21(2): 319-324

Szatmári T, Lumniczky K, Désaknai S, Trajcevski S, Hídvégi E J, Hamada H, Sáfrány G. Detailed characterization of the mouse glioma 261 tumor model for experimental glioblastoma therapy. *Cancer Sci.* 2006 June; 97(6):546-53

Teichert-Kuliszewska K, Maisonpierre P C, Jones N, Campbell A I, Master Z, Bendeck M P, Alitalo K, Dumont D J, Yancopoulos G D, Stewart D J. Biological action of angiopoietin-2 in a fibrin matrix model of angiogenesis is associated with activation of Tie2. *Cardiovasc Res.* 2001 Feb. 16; 49(3):659-70.

Thurston G, Rudge J S, Ioffe E, Zhou H, Ross L, Croll S D, Glazer N, Holash J, McDonald D M, Yancopoulos G D. Angiopoietin-1 protects the adult vasculature against plasma leakage. *Nat Med.* 2000 April; 6(4):460-3.

Tonnesen M G, Feng X, Clark R A (2000) Angiogenesis in wound healing. *J Investig Dermatol Symp Proc.* 5(1):40-6.

Tournaire R, Simon M P, le Noble F, Eichmann A, England P, Pouysségur J. (2004) A short synthetic peptide inhibits signal transduction, migration and angiogenesis mediated by Tie2 receptor. *EMBO Rep.;* 5(3):262-7.

Wang P, Xie Z H, Guo Y J, Zhao C P, Jiang H, Song Y, Zhu Z Y, Lai C, Xu S L, Bi J Z. VEGF-induced angiogenesis ameliorates the memory impairment in APP transgenic mouse model of Alzheimer's disease. *Biochem Biophys Res Commun.* 2011 Aug. 5; 411(3):620-6.

Yamanaka R. Medical management of brain metastases from lung cancer (Review). *Oncol Rep.* 2009 December; 22(6): 1269-76.

Yoon, J., Korkmaz, N., Han, S., Nam, C. and Chung, S. Self-vasculaizing three dimensional collagen by recombinant bacteriophages, 16th International Conference on Miniaturized Systems for Chemistry and Life Sciences, Okinawa, Japan, Oct. 28-Nov. 1, 2012.

Yuan Hai Tao, Eliyahu V. Khankin, S. Ananth Karumanchi, and Samir M. Parikh. Angiopoietin 2 Is a Partial Agonist/Antagonist of Tie2 Signaling in the Endothelium. *Mol Cell Biol.* 2009 April; 29(8): 2011-2022.

What is claimed is:

1. A method for treating cancer, comprising administering to a subject in need thereof an effective amount of a filamentous bacteriophage carrying bacterial Lipopolysaccharide (LPS) endotoxin on its surface in the form of a bacteriophage-LPS endotoxin complex, with the proviso that the filamentous bacteriophage does not display an antibody or a tumor specific peptide.

2. The method of claim 1, wherein the filamentous bacteriophage is a wild type, a wild type-like or a naturally occurring filamentous bacteriophage.

3. The method of claim 1, wherein the filamentous bacteriophage is selected from the group consisting of M13, fl, fd and mixtures thereof.

4. The method of claim 1, wherein the filamentous bacteriophage is administered by intranasal administration.

5. The method of claim 1, wherein the amount of bacterial LPS endotoxin carried on the filamentous bacteriophage is more than 100 endotoxin units/$2 \times 10^{12}$ bacteriophage or more than about 10 ng LPS/$2 \times 10^{12}$ bacteriophage.

6. The method of claim 1, wherein the amount of bacterial LPS endotoxin carried on the filamentous bacteriophage is about 430 endotoxin units/$1.7 \times 10^{12}$ bacteriophage.

7. The method of claim 1, wherein the cancer is a solid cancer selected from the group consisting of cancer of the brain, lung, stomach and other parts of the upper gastrointestinal tract, and the lower gastrointestinal tract.

8. The method of claim 7, wherein the cancer is glioblastoma.

9. The method of claim 7, wherein the solid cancer is liver cancer, cancer of the esophagus, colon cancer or rectal cancer.

10. The method of claim 1, wherein the filamentous bacteriophage-LPS endotoxin complex originates from *Escherichia coli*.

11. A method for treating cancer, comprising administering to a subject in need thereof an effective amount of a filamentous bacteriophage carrying bacterial Lipopolysaccharide (LPS) endotoxin on its surface in the form of a bacteriophage-LPS endotoxin complex and further displaying on its surface a peptide that binds to Tie2 receptor tyrosine kinase, with the proviso that the filamentous bacteriophage does not display an antibody or a tumor specific peptide.

12. The method of claim 11, wherein the filamentous bacteriophage is a wild type, a wild type-like or a naturally occurring filamentous bacteriophage.

13. The method of claim 11, wherein the filamentous bacteriophage is selected from the group consisting of M13, fl, fd and mixtures thereof.

14. The method of claim 11, wherein the filamentous bacteriophage is administered by intranasal administration.

15. The method of claim 11, wherein the amount of bacterial LPS endotoxin carried on the filamentous bacteriophage is more than 100 endotoxin units/$2 \times 10^{12}$ bacteriophage or more than about 10 ng LPS/$2 \times 10^{12}$ bacteriophage.

16. The method of claim 11, wherein the amount of bacterial LPS endotoxin carried on the filamentous bacteriophage is about 430 endotoxin units/$1.7 \times 10^{12}$ bacteriophage.

17. The method of claim 11, wherein the cancer is a solid cancer selected from the group consisting of cancer of the brain, lung, stomach and other parts of the upper gastrointestinal tract, and the lower gastrointestinal tract.

18. The method of claim 17, wherein the cancer is glioblastoma.

19. The method of claim 17, wherein the solid cancer is liver cancer, cancer of the esophagus, colon cancer or rectal cancer.

20. The method of claim 11, wherein the filamentous bacteriophage-LPS endotoxin complex originates from *Escherichia coli*.

21. The method of claim 11, wherein the filamentous bacteriophage displays on its surface a peptide comprising the amino acid sequence NLLMAAS (SEQ ID NO:1) as a peptide that binds to the Tie2 receptor.

* * * * *

SEQUENCE LISTING

```
<160> NUMBER OF SEQ ID NOS: 3

<210> SEQ ID NO 1
<211> LENGTH: 7
<212> TYPE: PRT
<213> ORGANISM: Artificial Sequence
<220> FEATURE:
<223> OTHER INFORMATION: synthetic

<400> SEQUENCE: 1
```

```
Asn Leu Leu Met Ala Ala Ser
1               5

<210> SEQ ID NO 2
<211> LENGTH: 12
<212> TYPE: PRT
<213> ORGANISM: Artificial Sequence
<220> FEATURE:
<223> OTHER INFORMATION: synthetic

<400> SEQUENCE: 2

Arg Arg Lys Arg Met Thr Ile Leu Lys Ser Arg Met
1               5                  10

<210> SEQ ID NO 3
<211> LENGTH: 12
<212> TYPE: PRT
<213> ORGANISM: Artificial Sequence
<220> FEATURE:
<223> OTHER INFORMATION: synthetic

<400> SEQUENCE: 3

Thr Arg Thr Lys Leu Pro Arg Leu His Leu Gln Ser
1               5                  10
```